(12) United States Patent
Johnson et al.

(10) Patent No.: US 8,108,042 B1
(45) Date of Patent: *Jan. 31, 2012

(54) CAPACITOR AND INDUCTOR ELEMENTS PHYSICALLY DISPOSED IN SERIES WHOSE LUMPED PARAMETERS ARE ELECTRICALLY CONNECTED IN PARALLEL TO FORM A BANDSTOP FILTER

(75) Inventors: Robert Shawn Johnson, North Tonawand, NY (US); Kishore Kumar Kondabatni, Williamsville, NY (US); Christopher Michael Williams, Lancaster, NY (US); Ryan Thomas Bauer, Plymouth, MN (US); Scott Brainard, Columbia Heights, MN (US); Qingshan Ye, Plymouth, MN (US); Warren S. Dabney, Orchard Park, NY (US); Robert A. Stevenson, Canyon Country, CA (US); Jeff Fleigle, Brooklyn Park, MN (US); Holly Noell Moschiano, Lancaster, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/273,658

(22) Filed: Oct. 14, 2011

Related U.S. Application Data

(63) Continuation of application No. 12/607,234, filed on Oct. 28, 2009, which is a continuation-in-part of application No. 11/860,402, filed on Sep. 24, 2007, now Pat. No. 7,853,324, and a continuation-in-part of application No. 11/558,349, filed on Nov. 9, 2006.

(60) Provisional application No. 61/109,672, filed on Oct. 30, 2008, provisional application No. 61/144,377, filed on Jan. 13, 2009.

(51) Int. Cl.
*A61N 1/00* (2006.01)
(52) U.S. Cl. .......................................................... 607/2
(58) Field of Classification Search ...................... 607/2
See application file for complete search history.

(56) References Cited

U.S. PATENT DOCUMENTS
3,871,382 A    3/1975  Mann
(Continued)

FOREIGN PATENT DOCUMENTS
EP    0243573    11/1987
(Continued)

OTHER PUBLICATIONS

Ariel Roguin et al., Modern Pacemaker and Implantable Cardioverter/Defibrillator Systems Can Be Magnetic Resonance Imaging Safe, Circulation—Journal of the American Heart Association, Aug. 4, 2004 (originally published online Jul. 26, 2004), pp. 475-482, American Heart Association, Dallas, Texas, USA.

(Continued)

*Primary Examiner* — George Manuel
(74) *Attorney, Agent, or Firm* — Michael F. Scalise

(57) ABSTRACT

One or more inductors and one or more capacitors are physically disposed relative to one another in series and are electrically connected to one another in parallel to form a bandstop filter. Chip inductors and chip capacitors having spaced apart conductive terminals are physically arranged in end-to-end abutting relation to minimize electrical potential between adjacent conductive terminals. The bandstop filter may be hermetically sealed within a biocompatible container for use with an implantable lead or electrode of a medical device. The values of the inductors and the capacitors are selected such that the bandstop filter is resonant at one or more selected frequencies, such as an MRI pulsed frequency.

20 Claims, 21 Drawing Sheets

U.S. PATENT DOCUMENTS

| | | | |
|---|---|---|---|
| 3,968,802 | A | 7/1976 | Ballis |
| 4,232,269 | A * | 11/1980 | Willoner .................. 330/85 |
| 4,633,181 | A | 12/1986 | Murphy-Boesch et al. |
| 4,654,880 | A | 3/1987 | Sontag |
| 4,689,621 | A | 8/1987 | Kleinberg |
| 4,799,499 | A | 1/1989 | Bisping |
| 4,858,623 | A | 8/1989 | Bradshaw et al. |
| 5,209,233 | A | 5/1993 | Holland et al. |
| 5,217,010 | A | 6/1993 | Tsitlik et al. |
| 5,246,438 | A | 9/1993 | Langberg |
| 5,300,108 | A | 4/1994 | Rebell et al. |
| 5,333,095 | A | 7/1994 | Stevenson et al. |
| 5,363,845 | A | 11/1994 | Chowdhury et al. |
| 5,398,683 | A | 3/1995 | Edwards et al. |
| 5,514,173 | A | 5/1996 | Rebell et al. |
| 5,545,201 | A | 8/1996 | Helland et al. |
| 5,629,622 | A | 5/1997 | Scampini |
| 5,697,958 | A | 12/1997 | Paul et al. |
| 5,716,390 | A | 2/1998 | Li |
| 5,722,998 | A | 3/1998 | Prutchi et al. |
| 5,741,321 | A | 4/1998 | Brennen |
| 5,751,539 | A | 5/1998 | Stevenson et al. |
| 5,759,202 | A | 6/1998 | Schroeppel |
| 5,905,627 | A | 5/1999 | Brendel et al. |
| 5,959,829 | A | 9/1999 | Stevenson et al. |
| 5,964,705 | A | 10/1999 | Truwit et al. |
| 5,973,906 | A | 10/1999 | Stevenson et al. |
| 5,978,204 | A | 11/1999 | Stevenson |
| 6,008,980 | A | 12/1999 | Stevenson et al. |
| 6,055,457 | A | 4/2000 | Bonner |
| 6,101,417 | A | 8/2000 | Vogel et al. |
| 6,141,594 | A | 10/2000 | Flynn et al. |
| 6,159,560 | A | 12/2000 | Stevenson et al. |
| 6,236,205 | B1 | 5/2001 | Ludeke et al. |
| 6,275,369 | B1 | 8/2001 | Stevenson et al. |
| 6,280,385 | B1 | 8/2001 | Melzer et al. |
| 6,424,234 | B1 | 7/2002 | Stevenson |
| 6,456,481 | B1 | 9/2002 | Stevenson |
| 6,473,291 | B1 | 10/2002 | Stevenson |
| 6,493,591 | B1 | 12/2002 | Stokes |
| 6,529,103 | B1 | 3/2003 | Brendel et al. |
| 6,535,766 | B1 | 3/2003 | Thompson et al. |
| 6,539,253 | B2 | 3/2003 | Thompson et al. |
| 6,566,978 | B2 | 5/2003 | Stevenson et al. |
| 6,567,259 | B2 | 5/2003 | Stevenson et al. |
| 6,567,703 | B1 | 5/2003 | Thompson et al. |
| 6,643,903 | B2 | 11/2003 | Stevenson et al. |
| 6,675,033 | B1 | 1/2004 | Lardo et al. |
| 6,675,779 | B2 | 1/2004 | King et al. |
| 6,675,780 | B1 | 1/2004 | Wendels et al. |
| 6,687,550 | B1 | 2/2004 | Doan |
| 6,701,176 | B1 | 3/2004 | Halperin et al. |
| 6,765,780 | B2 | 7/2004 | Brendel et al. |
| 6,847,837 | B1 | 1/2005 | Melzer et al. |
| 6,868,288 | B2 | 3/2005 | Thompson |
| 6,876,885 | B2 | 4/2005 | Swoyer et al. |
| 6,882,248 | B2 | 4/2005 | Stevenson et al. |
| 6,898,454 | B2 | 5/2005 | Atalar et al. |
| 6,925,328 | B2 | 8/2005 | Foster et al. |
| 6,931,286 | B2 | 8/2005 | Sigg et al. |
| 6,949,929 | B2 | 9/2005 | Gray et al. |
| 6,952,613 | B2 | 10/2005 | Swoyer et al. |
| 6,971,391 | B1 | 12/2005 | Wang et al. |
| 6,985,347 | B2 | 1/2006 | Stevenson et al. |
| 6,999,818 | B2 | 2/2006 | Stevenson et al. |
| 7,013,180 | B2 | 3/2006 | Villaseca et al. |
| 7,092,766 | B1 | 8/2006 | Salys et al. |
| 7,113,387 | B2 | 9/2006 | Stevenson et al. |
| 7,155,271 | B2 | 12/2006 | Halperin |
| 7,920,916 | B2 * | 4/2011 | Johnson et al. .................. 607/2 |
| 2003/0028094 | A1 | 2/2003 | Kumar et al. |
| 2003/0050557 | A1 | 3/2003 | Susil et al. |
| 2003/0144720 | A1 | 7/2003 | Villaseca et al. |
| 2004/0167392 | A1 | 8/2004 | Halperin et al. |
| 2004/0263173 | A1 | 12/2004 | Gray |
| 2004/0263174 | A1 | 12/2004 | Gray et al. |
| 2005/0197677 | A1 | 9/2005 | Stevenson |
| 2006/0009819 | A1 | 1/2006 | Przybyszewski |
| 2006/0100506 | A1 | 5/2006 | Halperin et al. |

FOREIGN PATENT DOCUMENTS

| | | |
|---|---|---|
| EP | 0145430 | 5/1991 |
| EP | 0498996 | 3/1997 |
| EP | 0930509 | 12/1998 |
| EP | 1021730 | 4/1999 |
| JP | 60141034 | 7/1985 |
| JP | 61181925 | 8/1985 |
| JP | 62233905 | 10/1987 |
| JP | 4071536 | 3/1992 |
| JP | 6054823 | 3/1994 |
| JP | 11239572 | 9/1999 |
| WO | 99/19739 | 4/1999 |
| WO | 02/083016 | 10/2002 |

OTHER PUBLICATIONS

Roger Christoph Luchinger, Safety Aspects of Cardiac Pacemakers in Magnetic Resonance Imaging, a dissertation submitted to the Swiss Federal Institute of Technology Zurich, Zurich, Switzerland, 2002.

C. Gabriel, S. Gabriel and E. Cortout, I. Dielectric Properties of Biological Tissues: Literature Survey, 1996.

S. Gabriel, R.W. Lau and C. Gabriel, II. Dielectric Properties of Biological Tissues: Measurements and the Frequency Range 0Hz to 20 GHz, 1996.

S. Gabriel, R.W. Lau and C. Gabriel, III. Dielectric Properties of Biological Tissues: Parametric Models for the Dielectric Spectrum of Tissues, 1996.

Constantine A. Balanis, Advanced Engineering Electromagnetics, John Wiley & Sons, Inc., 1989.

Robert C. Susil, Christopher J. Yeung, Henry R. Halperin, Albert CL. Lardo, Ergin Atalar, Multifunctional Interventional Devices for MRI: A Combined Electrophysiology/MRI Catheter, Magnetic Resonance in Medicine, 2002, pp. 594-600, Wiley-Liss, Inc., Departments of Biomedical Engineering, Radiology & Medicine, Johns Hopkins University School of Medicine, Baltimore, Maryland.

Robert C. Susil, Ergin Atalar, Albert Lardo, Multifunctional Interventional Devices for Use in MRI, U.S. Appl. No. 60/283,725, filed Apr. 13, 2001.

* cited by examiner

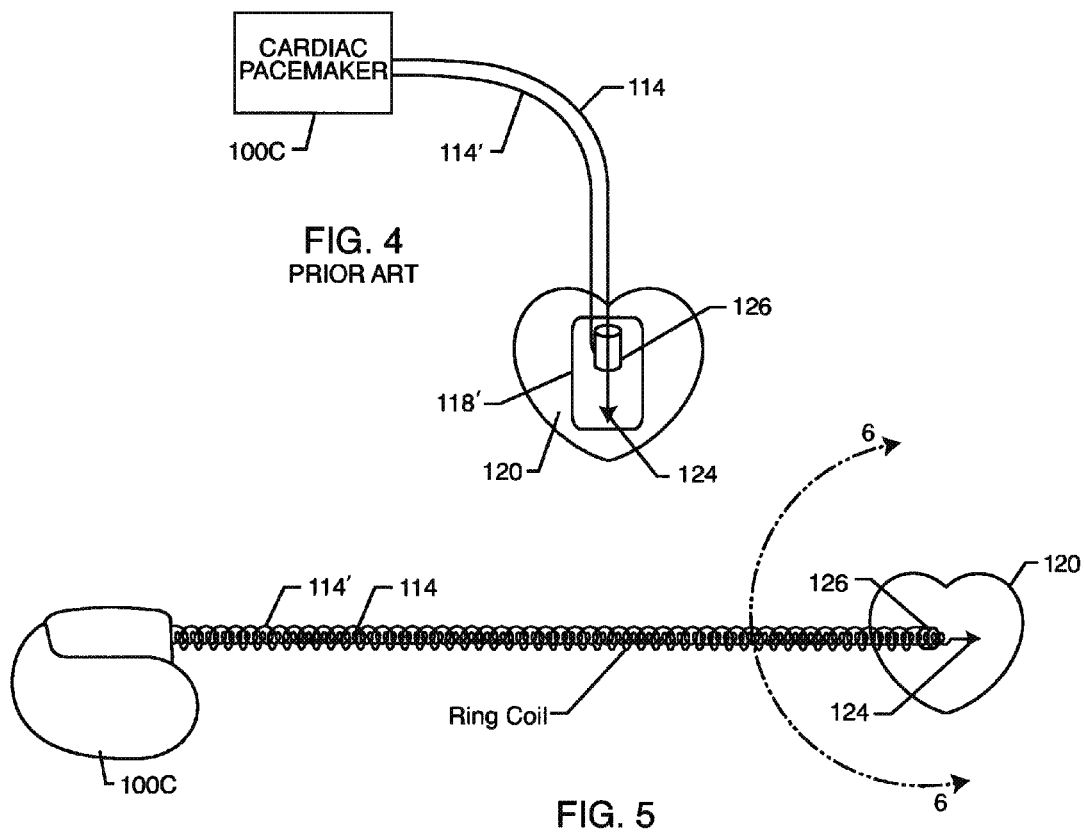
FIG. 4
PRIOR ART
FIG. 5
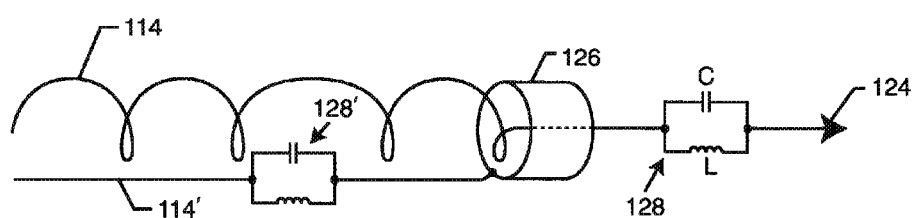
FIG. 6

CAPACITOR AND INDUCTOR ELEMENTS PHYSICALLY DISPOSED IN SERIES WHOSE LUMPED PARAMETERS ARE ELECTRICALLY CONNECTED IN PARALLEL TO FORM A BANDSTOP FILTER

CROSS REFERENCE TO RELATED APPLICATIONS

This application is a continuation of U.S. application Ser. No. 12/607,234, filed on Oct. 28, 2009, which is a continuation-in-part of application Ser. No. 11/860,402, filed Sep. 24, 2007 now U.S. Pat. No. 7,853,324 and a continuation-in-part of application Ser. No. 11/558,349, filed on Nov. 9, 2006 and which claims priority from U.S. provisional application No. 61/109,672, filed on Oct. 30, 2008 and provisional application No. 61/144,377, filed on Jan. 13, 2009.

FIELD OF INVENTION

The present invention relates to passive bandstop filter circuits wherein one or more of both inductor (L) and capacitor (C) elements are physically disposed in series but whose equivalent (lumped) L-C parameters are electrically connected in parallel. These novel L-C bandstop filters may be wired in series or in parallel with the leads or circuit traces of electronic circuits as needed for the particular application, for example, military, space, medical, commercial electronics, aviation or other applications. More specifically, the present invention is particularly suitable for applications where it is important to keep the diameter or cross-sectional area of the bandstop filter relatively small. A particular application of the invention is directed to the bandstop filter being installed in series with medical implanted leads in order reduce the amount of radio frequency (RF) current and associated heating due to energy deposited on the leads during medical diagnostic procedures, such as magnetic resonance imaging (MRI). The bandstop filter is designed to be resonant at the MRI RF pulsed frequency and thereby present a high impedance in the lead thus reducing RF current flow. Reduction of MRI induced RF current in an implanted lead prevents dangerous overheating and the associated possibility of damage to adjacent tissues.

BACKGROUND OF THE INVENTION

This invention generally relates to the problem of energy induced into implanted leads during medical diagnostic procedures such as magnetic resonant imaging (MRI). Specifically, the RF pulsed field of MRI equipment can couple to an implanted lead in such a way that electromagnetic forces (EMFs) are induced in the lead. The amount of energy that is induced is related to a number of complex factors, but in general is dependent upon the local electric field that is tangent to lead and the integral of the electric field strength along the lead. In certain situations, these EMFs can cause currents to flow into distal electrodes or in the electrode interface with body tissue. It has been documented that when this current becomes excessive, overheating of said electrode or overheating of the associated interface with body tissue can occur. There have been cases of damage to such body tissue which has resulted in loss of capture of cardiac pacemaking pulses, tissue damage severe enough to result in brain damage or multiple amputations, and the like.

Implantable lead systems are generally associated with active implantable medical devices (AIMDs) such as cardiac pacemakers, cardioverter defibrillators, neurostimulators and the like. Implantable leads can also be associated with external devices such as external pacemakers, externally worn neurostimulators (such as pain control spinal cord stimulators) and the like.

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific (formerly Guidant), one will see that the use of MRI is generally contra-indicated with pacemakers and implantable defibrillators.

However, an extensive review of the literature indicates that MRI is indeed often used with pacemaker, neurostimulator and other active implantable medical device (AIMD) patients. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker patients means that pacemaker and implantable cardioverter defibrillator (ICD) wearers are excluded from MRI. This is particularly true of scans of the thorax and abdominal areas. Because of MRI's incredible value as a diagnostic tool for imaging organs and other body tissues, many physicians simply take the risk and perform MRI on a pacemaker patient. The literature indicates a number of precautions that physicians should take in this case, including limiting the power of the MRI RF pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leadwires or devices. For example, for magnetic resonance imaging devices operating at the same magnetic field strength and also at the same SAR level, considerable variations have been found relative to heating of implanted leadwires. It is speculated that SAR level alone is not a good predictor of whether or not an implanted device or its associated leadwire system will overheat.

There are three types of electromagnetic fields produced by MRI equipment. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. Certain research systems are as high as 11.7 Tesla. This is over 100,000 times the magnetic field strength of the earth. A static magnetic field can induce powerful mechanical forces and torque on any magnetic materials implanted within the patient. This would include certain components within the cardiac pacemaker itself and/or lead systems. It is not likely (other than sudden system shut down) that the static MRI magnetic field can induce currents into the pacemaker lead system and hence into the pacemaker itself. It is a basic principle of physics that a magnetic field must either be time-varying as it cuts across the conductor, or the conductor itself must move within the magnetic field for currents to be induced.

The second type of field produced by magnetic resonance imaging is the pulsed RF field, designated $B_1$, which is generated by the body coil or head coil. This is used to change the energy state of the protons and elicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during scanning protocols and usually has a frequency of 21 MHz to 64 MHz to 128 MHz depending upon the static magnetic field strength. The frequency of the RF pulse varies by the Lamor equation with the field strength of the main static field where: RF PULSED FREQUENCY in MHz=(42.56) (STATIC FIELD STRENGTH IN TESLA).

The third type of MRI electromagnetic field is the time-varying magnetic gradient fields designated $G_x$, $G_y$, $G_z$ which are used for spatial localization. These change their strength along different orientations and operating frequencies on the order of 1 to 2 kHz. The vectors of the magnetic field gradients in the x, y and z directions are produced by three sets of orthogonally positioned coils and are switched on only during the scanning protocols.

At very low frequency (VLF), voltages are induced at the input to the cardiac pacemaker as currents circulate throughout the patient's body and create voltage drops. Because of the vector displacement between the pacemaker housing and, for example, the Tip electrode, voltage drop across the resistance of body tissues may be sensed due to Ohm's Law and the circulating current of the RF signal. At higher frequencies, the implanted lead systems actually act as antennas where voltages (EMFs) are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the lead system (for example, at the header block of a cardiac pacemaker). This has to do with the wavelength of the signals involved and where they couple efficiently into the system.

MRI gradient field coupling into an implanted lead system is based on loop areas and orientation. For example, in a cardiac pacemaker unipolar lead, there is a loop formed by the lead as it comes from the cardiac pacemaker housing to its distal tip, for example, located in the right ventricle. The return path is through body fluid and tissue generally from the Tip electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal implant, the implanted loop area is much larger (approximately 377 square centimeters). Relating now to the specific case of MRI, the magnetic gradient fields would be induced through enclosed loop areas. However, the pulsed RF fields, which are generated by the body coil, would be primarily induced into the lead system by antenna action.

At the frequencies of interest in MRI, RF energy can be absorbed and converted to heat. The cause of heating in an MRI environment is twofold: (a) RF field coupling to the lead can occur which induces significant local heating; and (b) currents induced between the distal tip and tissue during MRI RF pulse transmission sequences can cause local ohmic heating in tissue next to the distal Tip electrode of the implanted lead. The power deposited by RF pulses during MRI is complex and is dependent upon the power (Specific Absorption Rate (SAR)) level and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and its associated lead(s). For example, it will make a difference how much EMF is induced into a pacemaker lead system as to whether it is a left or right pectoral implant. In addition, the routing of the lead and the lead length are also very critical as to the amount of induced current and heating that would occur. Also, distal Tip electrode design is very important as the distal Tip electrode itself can act as its own antenna wherein eddy currents can create heating. The RF field of an MRI scanner can produce enough energy to induce lead RF voltages and resulting currents sufficient to destroy some of the adjacent myocardial tissue. Tissue ablation has also been observed. The effects of this heating are not readily detectable by monitoring during the MRI scan. Indications that heating has occurred would include an increase in pacing threshold, venous ablation, Larynx or esophageal ablation, myocardial perforation and lead penetration, or even arrhythmias caused by scar tissue. However, these effects are typically determined some time after the scan is completed. Such long term heating effects of MRI have not been well studied yet for all types of AIMD lead geometries. There can also be localized heating problems associated with various types of electrodes in addition to Tip electrodes. This includes Ring electrodes or Pad electrodes. Ring electrodes are commonly used with a wide variety of implanted devices including cardiac pacemakers, neurostimulators and the like. Pad electrodes are very common in neurostimulator applications. For example, spinal cord stimulators or deep brain stimulators can include a plurality of Pad electrodes to make contact with nerve tissue. A good example of this also occurs in a cochlear implant. In a typical cochlear implant there would be sixteen Ring electrodes placed up into the cochlea. Several of these Ring electrodes make contact with auditory nerves.

Although there are a number of studies that have shown that MRI patients with active implantable medical devices, such as cardiac pacemakers, can be at risk for potential hazardous effects, there are a number of reports in the literature that MRI can be safe for imaging of pacemaker patients when a number of precautions are taken (only when an MRI is thought to be an absolute diagnostic necessity). While these anecdotal reports are of interest, they are certainly not scientifically convincing that all MRI can be safe. For example, just variations in the pacemaker lead length can significantly affect how much heat is generated. A paper entitled, HEATING AROUND INTRAVASCULAR GUIDEWIRES BY RESONATING RF WAVES by Konings, et al., Journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the function of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each manufacturer's pacemaker and ICD designs also are designed and behave differently. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal Tip (or Ring) electrodes. This can lead to overheating of body tissue at or adjacent to the distal Tip electrode.

Distal Tip electrodes can be unipolar, bipolar and the like. It is very important that excessive current not flow at the interface between the distal Tip electrode and body tissue. In a typical cardiac pacemaker, for example, the distal Tip electrode can be passive or of a screw-in helix type. In any event, it is very important that excessive RF current not flow at this junction between the distal Tip electrode and for example, myocardial or nerve tissue. This is because tissue damage in this area can raise the capture threshold or completely cause loss of capture. For pacemaker dependent patients, this would mean that the pacemaker would no longer be able to pace the heart. This would, of course, be life threatening for a pacemaker dependent patient. For neurostimulator patients, such as deep brain stimulator patients, the ability to have an MRI is equally important.

The most important and most life-threatening item is to be able to control overheating of implanted leads during an MRI procedure. A novel and very effective approach to this is to install parallel resonant inductor and capacitor bandstop filters at or near the distal electrode of implanted leads, as described in U.S. Pat. No. 7,363,090, and U.S. Patent Publication Nos. US 2007/0112398 A1; US 2008/0071313 A1; US 2008/0049376 A1; US 2008/0161886 A1; US 2008/0132987 A1; US 2008/0116997 A1; and US 2009/0163980 A1 the contents all of which are incorporated herein. US 2007/0112398 A1 relates generally to L-C bandstop filter assemblies, particularly of the type used in active implantable medical devices (AIMDs) such as cardiac pacemakers, cardioverter defibrillators, neurostimulators and the like, which raise the impedance of internal electronic or related wiring components of the medical device at selected frequencies in order to reduce or eliminate currents induced from undesirable electromagnetic interference (EMI) signals.

U.S. Pat. No. 7,363,090 and US 2007/0112398 A1 disclose resonant L-C bandstop filters to be placed at the distal tip and/or at various locations along the medical device leadwires or circuits. These bandstop filters inhibit or prevent current from circulating at selected frequencies of the medical therapeutic device. For example, for an MRI system operating at 1.5 Tesla, the pulsed RF frequency is 63.8 MHz, as shown by the Lamour Equation. The bandstop filter can be designed to resonate at or near 64 MHz and thus create a high impedance (ideally an open circuit) in the lead system at that selected frequency. For example, the bandstop filter, when placed at the distal tip of a pacemaker leadwire, will significantly reduce RF currents from flowing through the distal tip and into body tissue. It will be obvious to those skilled in the art that all of the embodiments described in U.S. Pat. No. 7,363,090 are equally applicable to a wide range of other implantable and external medical devices, including deep brain stimulators, spinal cord stimulators, drug pumps, probes, catheters and the like.

Electrically engineering a capacitor in parallel with an inductor is known as a tank circuit or bandstop filter. It is well known that when a near-ideal bandstop filter is at its resonant frequency, it will present a very high impedance. Since MRI equipment produces very large RF pulsed fields operating at discrete frequencies, this is an ideal situation for a specific resonant bandstop filter. Bandstop filters are more efficient for eliminating one single frequency than broadband filters. Because the bandstop filter is targeted at this one frequency, it can be much smaller and volumetrically efficient.

However, a major challenge when designing a bandstop filter for human implant is that it must be very small in size, biocompatible, and highly reliable. Coaxial geometry is preferred. The reason that a coaxial geometry is preferred is that leads are placed at locations in the human body primarily by one of two main methods. The first is guide wire endocardial lead insertion. For example, in a cardiac pacemaker application, a pectoral pocket is created and then the physician makes a small incision and accesses the cephalic or subclavian vein. The endocardial pacemaker leads are stylus guided/routed down through this venous system through the right atrium, through the tricuspid valve and into, for example, the right ventricle. A second primary method of installing leads (particularly for neurostimulators) in the human body is by tunneling. In tunneling, a surgeon uses special tools to tunnel under the skin and through the muscle, for example, up through the neck to access the Vagus nerve or the deep brain. In both techniques, it is very important that the leads and their associated electrodes at the distal tips be very small.

Accordingly, there is a need for a bandstop filter for medical devices, and particularly human implanted devices and components thereof, which is very small in size, biocompatible, and highly reliable. There is also a need for such a bandstop filter which can be placed coaxially relative to a leadwire or electrode of a lead system. The present invention fulfills these needs, and provides other related advantages.

SUMMARY OF THE INVENTION

The present invention relates to passive bandstop filter circuits wherein one or more of both inductor (L) and capacitor (C) elements are physically disposed in series but whose equivalent (lumped) LC parameters are electrically connected in parallel. More particularly, the bandstop filter comprises an inductor having first and second conductive terminals in spaced non-conductive relation, and a capacitor having first and second conductive terminals in spaced non-conductive relation, wherein the inductor and the capacitor are physically disposed in series relative to one another, and wherein the inductor and the capacitor are electrically connected to one another in parallel.

In the illustrated embodiments, one of the first or second conductive terminals of the inductor is disposed generally adjacent to one of the first or second conductive terminals of the capacitor. Such an arrangement results in the capacitor and the inductor being aligned along a common axis. In preferred embodiments, the adjacent conductive terminals of the inductor and the capacitor abut one another. However, if the electrical potential of the adjacent surfaces has not been minimized or zeroed, an electrical insulator may be disposed between the adjacent conductive terminals of the inductor and the capacitor.

As illustrated herein, the inductor comprises a chip inductor, and the capacitor comprises a chip capacitor. The second conductive terminal of the inductor is preferably conductively coupled to the first conductive terminal of the capacitor, and the first conductive terminal of the inductor is conductively coupled to the second conductive terminal of the capacitor, all the while the inductor and the capacitor being physically disposed in series relative to one another.

The parallel capacitor and inductor may be disposed in series in an electrical lead or circuit trace. The capacitor and the inductor may be tuned to impede induced current flow through the electrical lead at a selected frequency. Typically, the electrical lead comprises a portion of an implanted lead for a medical device. The electrical lead may include an active fixation tip, wherein the bandstop filter is disposed within the active fixation tip.

The bandstop filter may further comprise a plurality of paired inductors and capacitors, wherein in each paired inductor and capacitor, the inductor and the capacitor are physically disposed in series relative to one another and yet electrically connected to one another in parallel. Each paired inductor and capacitor may further be electrically connected in series to another paired inductor and capacitor.

In another embodiment, the parallel capacitor and inductor are disposed in parallel between two electrical leads or circuit traces. The capacitor and the inductor are tuned to divert induced current flow through the electrical leads except at a selected frequency.

The capacitor and the inductor may be comprised of biocompatible and non-migratable materials. In particular, the inductor, the capacitor, and all associated electrical connections, and support substrates, if any, may comprise biocompatible materials to form a biocompatible package suitable for mammalian implantation. However, when elements of the capacitor and/or the inductor comprise non-biocompatible materials, they may be disposed within a hermetically sealed container. In this case, the hermetically sealed container comprises a biocompatible housing in which the bandstop filter is disposed, and biocompatible first and second conductive contacts extending through the housing which are conductively coupled in series to the bandstop filter. In medical implant applications, the hermetically sealed container may be disposed in series in the electrical lead, and the first and second contacts may be connected to, respectively, first and second portions of the lead. In a related assembly process, a substrate is provided onto which the inductor and the capacitor are fixed in a pre-assembly prior to insertion into the biocompatible housing. The pre-assembly is tested prior to insertion into the biocompatible housing, and after the pre-assembly is inserted into the biocompatible housing, hermetical terminals comprising at least a portion of the first and second conductive contacts are hermetically sealed to the housing.

In several of the illustrated embodiments, the inductor comprises a plurality of inductors which may be conductively coupled to one another either in series or in parallel. However, in accordance with the present invention, the plurality of inductors are physically disposed in series relative to one another. In a similar manner, the capacitor may comprise a plurality of capacitors conductively coupled to one another either in series or in parallel. Again, in accordance with the present invention, the plurality of capacitors is physically disposed in series relative to one another.

The values of the inductor and the capacitor are selected such that the bandstop filter is resonant at a selected frequency. The overall Q of the bandstop filter is selected to balance impedance at the selected frequency versus frequency bandwidth characteristics. This may be accomplished when the Q of the inductor is relatively high and the Q of the capacitor is relatively low, such as when the inductor has a relatively low resistive loss and when the capacitor has a relatively high equivalent series resistance. Alternatively, this may also be accomplished when the Q of the inductor is relatively low and the Q of the capacitor is relatively high, which is accomplished when the inductor has a relatively high resistive loss and the capacitor has a relatively low equivalent series resistance. The selected frequency may comprise an MRI pulsed frequency, and the overall Q of the bandstop filter may be selected to attenuate current flow along a lead or circuit trace through a range of selected frequencies.

The inductor and the capacitor may be mounted on a flexible substrate, which itself may include portions that are wrapped around the capacitor and the inductor during the assembly process. Typically, such a wrapped assembly is disposed within a protective container such as a hermetically sealed biocompatible housing.

In an illustrated embodiment, the inductor is disposed on a first surface of an intermediate substrate, and the capacitor is disposed on a second generally opposite surface of the intermediate substrate. Circuit traces extend through the intermediate substrate and conductively couple the inductor and the capacitor in parallel. Of course, all of the aforementioned assemblies may be formed utilizing robotic manufacturing techniques wherein the inductor and the capacitor are robotically deposited on the substrate. The substrate itself may comprise a multi-layered flex cable Finally, in yet another illustrated embodiment, the capacitor comprises a feedthrough capacitor and the inductor comprises a chip inductor. In accordance with the present invention, the chip inductor and the feedthrough capacitor are physically disposed in series but the equivalent (lumped) LC parameters are electrically connected in parallel to form a bandstop filter. The chip inductor and the feedthrough capacitor may be disposed within a biocompatible housing; however, in comparison with other embodiments, only a single hermetic seal assembly is required thus reducing costs.

All of the illustrated embodiments are suitable for use with ultra-miniature inductor and capacitor chip components that are mechanically installed in hermetic packages in series, but have electrical circuit traces that put the components electrically in parallel, to form the desired bandstop filter having tank circuit characteristics.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 4 is a schematic illustration of a bipolar leadwire system with a distal Tip and ring typically as used with a cardiac pacemaker.

FIG. 5 is a schematic illustration of a prior art single chamber bipolar cardiac pacemaker lead showing the distal Tip and the distal Ring electrodes.

FIG. 6 is an enlarged, fragmented schematic view taken generally along the line 6-6 of FIG. 5, illustrating placement of bandstop filters adjacent to the distal tip and Ring electrodes.

DETAILED DESCRIPTION OF THE PREFERRED EMBODIMENTS

As shown in the accompanying drawings for purposes of illustration, the present invention is directed to miniature inductor and chip components which are physically arranged in series, but electrically connected to one another in parallel to form tank circuits and bandstop filters for impeding or diverting currents induced by electromagnetic interference, for example, in a lead or an electrode of a medical device. Such bandstop filters may be placed electrically in series with an implanted lead or electrode of an active implantable medical device (AIMD), and in a variety of other electronics circuits used in commercial electronics, military, aerospace or other applications, where it may serve as an impeder at certain resonant frequencies. The bandstop filter of the present invention may also be placed electrically in parallel between leads or circuit traces where it may serve as a RF current diverter at the resonant frequency.

Figure 1:
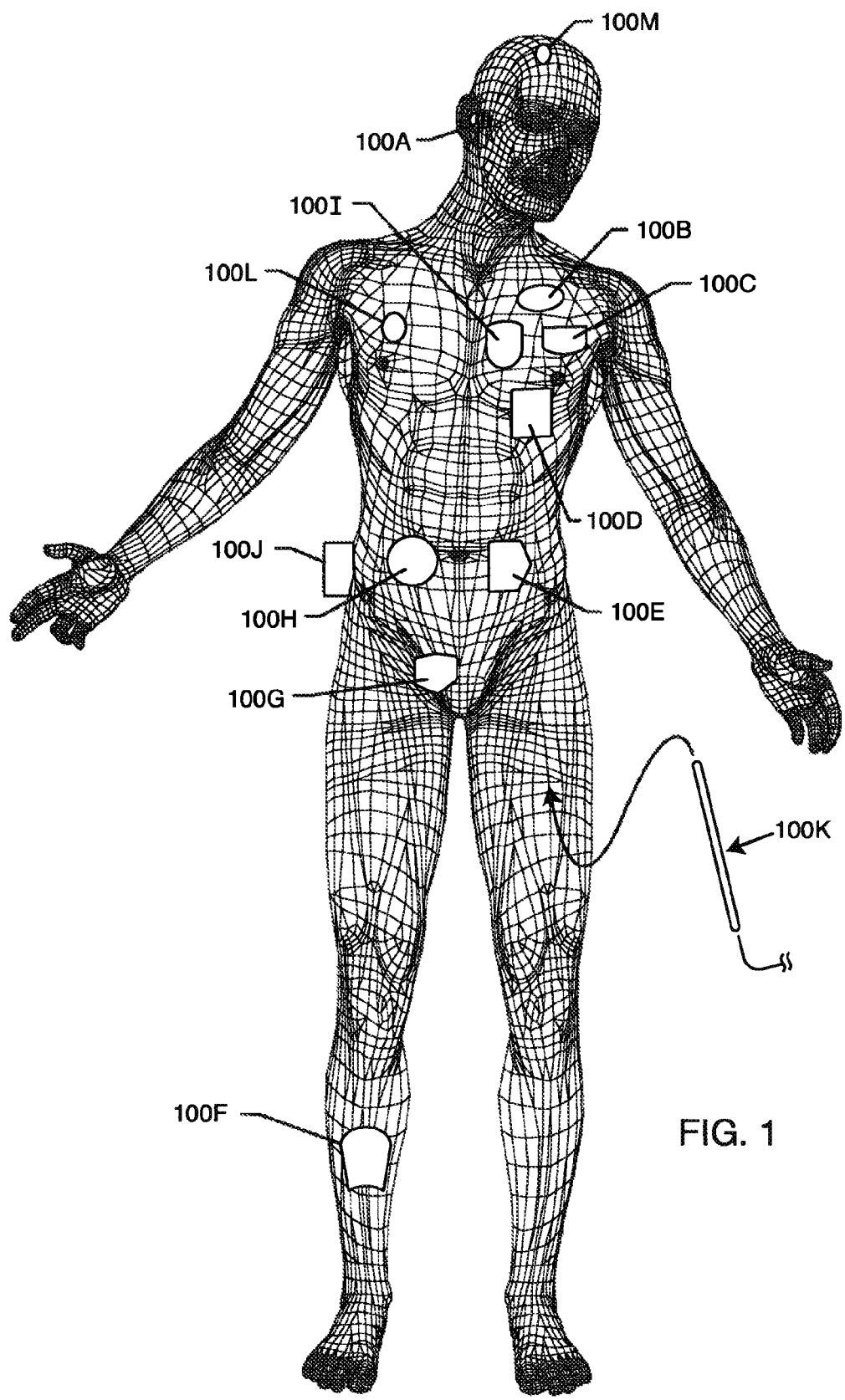
FIG. 1 is a wire-formed diagram of a generic human body showing a number of exemplary medical devices.

FIG. 1 is a wire formed diagram of a generic human body showing a number of active implantable and external medical devices 100 that are currently in use. 100A represents a family of hearing devices which can include the group of cochlear implants, piezoelectric sound bridge transducers and the like. 100B represents a variety of neurostimulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent the seizure from actually occurring. The leads associated with a deep brain stimulator are often placed using real time MRI imaging. Most commonly such leads are placed during real time MRI. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator or even a ventricular assist device. 100K illustrates the insertion of an external probe or catheter. These probes can be inserted into the femoral artery, for example, or in any other number of locations in the human body. 100L illustrates one of various types of EKG/ECG external skin electrodes which can be placed at various locations. 100M are external EEG electrodes placed on the head.

Figure 2:
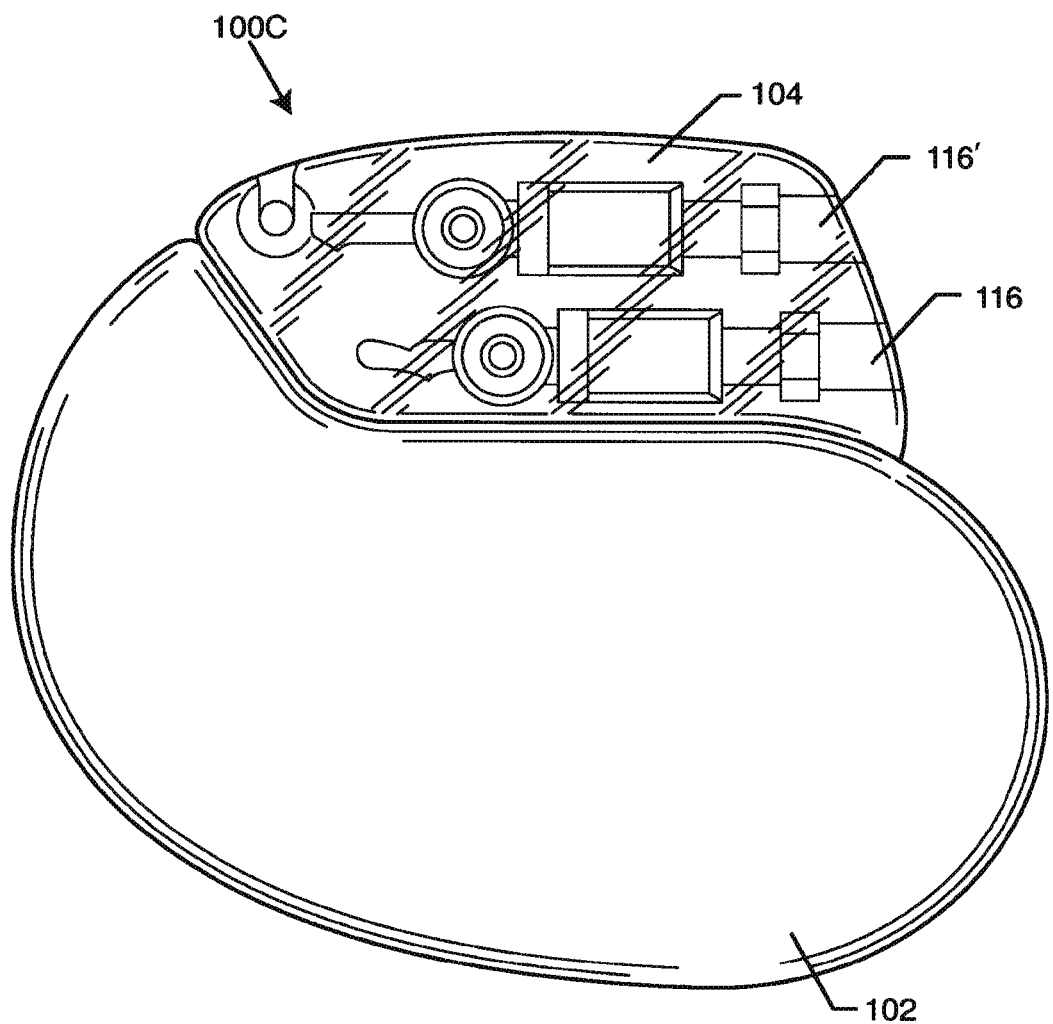
FIG. 2 is an elevational view of a typical prior art cardiac pacemaker showing the metal case and an IS-1 header block.
Figure 3:
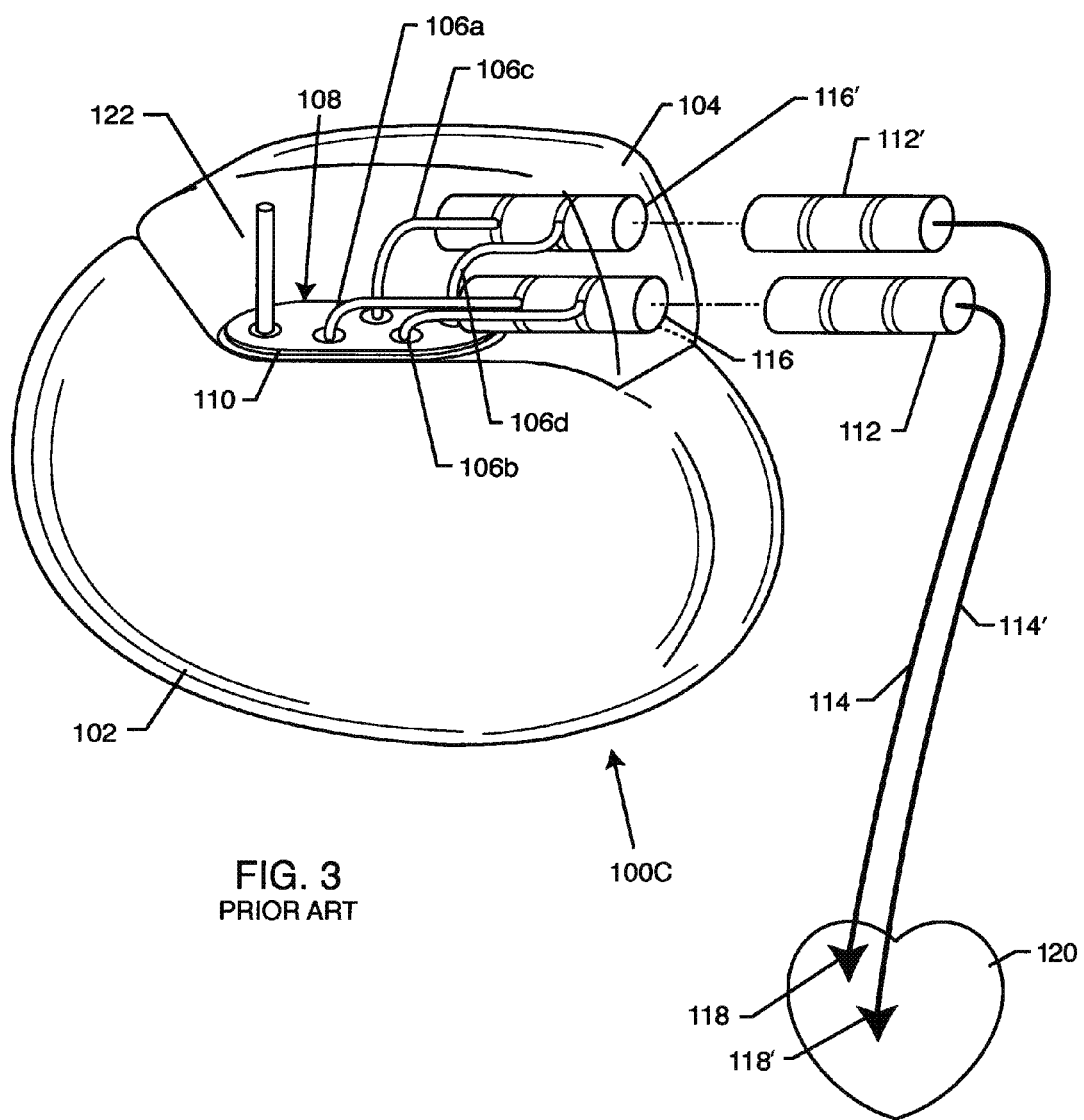
FIG. 3 is a perspective view of the cardiac pacemaker of FIG. 2, with exemplary associated leads to the heart.

FIGS. 2 and 3 are drawings of a typical cardiac pacemaker 100C showing a titanium case or housing 102 and an IS-1 header connector block 104. The titanium case or housing 102 is hermetically sealed, however there is a point where leadwires 106 must ingress and egress a hermetic seal. This is accomplished by providing a hermetic terminal assembly 108 that generally consists of a ferrule 110 which is laser welded to the titanium housing 102 of the AIMD 100C.

Referring to FIG. 3, four leadwires are shown consisting of leadwire pair 106a and 106b and leadwire pair 106c and 106d. This is typical of what is known as a dual chamber bipolar cardiac pacemaker. The IS-1 connectors 112 and 112' of leads 114 and 114' are designed to plug into receptacles 116 and 116' in the header block 104. The receptacles 116 and 116' are low voltage (pacemaker) connectors covered by an ANSI/AAMI ISO standard IS-1. Higher voltage devices, such as implantable cardioverter defibrillators (ICDs), are covered by ANSI/AAMI ISO standard DF-1. A new standard which will integrate both high voltage and low voltage connectors into a miniature in-line quadripolar connector is known as the IS-4 series. The implanted leads 114 and 114' are typically routed in a pacemaker application down into the right atrium 118 and the right ventricle 118' of the heart 120. New generation biventricular devices may introduce leads to the outside of the left ventricle, which devices have proven to be very effective in cardiac resynchronization and treating congestive heart failure (CHF).

An RF telemetry pin antenna 122 is also shown which is not electrically connected to the leadwires 106 or the receptacles 116. The RF telemetry pin antenna 122 acts as a short stub antenna for picking up telemetry (programming) signals that are transmitted from the outside of the device 100C.

Although the present invention will be described herein in the context and environment of a cardiac pacemaker 100C and its associated leads 114, the present invention may also be advantageously utilized in many other types of AIMDs as briefly outlined above, as well as in other commercial electronic, military, aerospace and other applications. In the following discussion, to the extent practicable, functionally equivalent components will retain the same or a similar (in increments of 100) reference number, irrespective of the particular embodiment being described.

FIG. 4 illustrates a prior art single chamber bipolar device 100C and lead system 114 and 114' with a distal Tip electrode 124 and a Ring electrode 126 typically as used with the cardiac pacemaker 100C. Should the patient be exposed to the fields of an MRI scanner or other powerful emitter used during a medical diagnostic procedure, currents that are directly induced in the lead system 114 can cause heating by $I^2R$ losses in the lead system or by heating caused by RF current flowing from the Tip and Ring electrodes 124, 126 into body tissue. If these induced RF currents become excessive, the associated heating can cause damage or even destructive ablation to body tissue.

FIG. 5 illustrates a single chamber bipolar cardiac pacemaker 100C, and leads 114 and 114' having distal Tip 124 and distal Ring 126 electrodes. This is a spiral wound (coaxial) system where the Ring coil 114' is wrapped around the Tip coil 114. There are other types of pacemaker leadwire systems in which these two leads lay parallel to one another (known as a bifilar lead system), which are not shown.

FIG. 6 is an enlarged schematic illustration of the area "6-6" in FIG. 5. In the area of the distal Tip 124 and Ring 126 electrodes, bandstop filters 128 and 128' have been placed in series with each of the respective Ring and Tip circuits. The Ring circuit wire 114' has been drawn straight instead of coiled for simplicity. The bandstop filters 128 and 128' are tuned such that, at an MRI pulsed RF frequency, a high impedance will be presented thereby reducing or stopping the flow of undesirable MRI induced RF current from the electrodes 124 and 126 into body tissues.

The Tip electrode 124 is designed to be inserted into intimate contact with myocardial tissue. Over time it becomes encapsulated and fully embedded or buried within such tissue. However, the Ring electrode 126 is designed to float within the blood pool, for example, in the ventricle 118' or atrium 118. With the constant blood perfusion, the Ring electrode 126 is somewhat cooled during medical diagnostic procedures, such as MRI. However, the Tip electrode 124, which is embedded in the myocardial tissue, is thermally insulated in comparison. Moreover, it can't always be assumed that a Ring electrode 126 that is floating in the blood pool will be adequately cooled by the flow of blood. There are certain types of patients that have cardiovascular diseases that lead to very low blood flow rates and perfusion issues. The Ring electrode 126 can also become encapsulated by body tissues. Accordingly, both the distal Tip electrode 124 and the Ring electrode 126 are preferably both associated with bandstop filters 128 and 128'. However, since the operation of the bandstop filter 128 is more important with the Tip electrode 124 than it is with the Ring electrode 126 in order to prevent distal tip heating and associated tissue damage, in many cardiac applications only a Tip bandstop filter 128 may be required for MRI compatibility.

Figure 7:
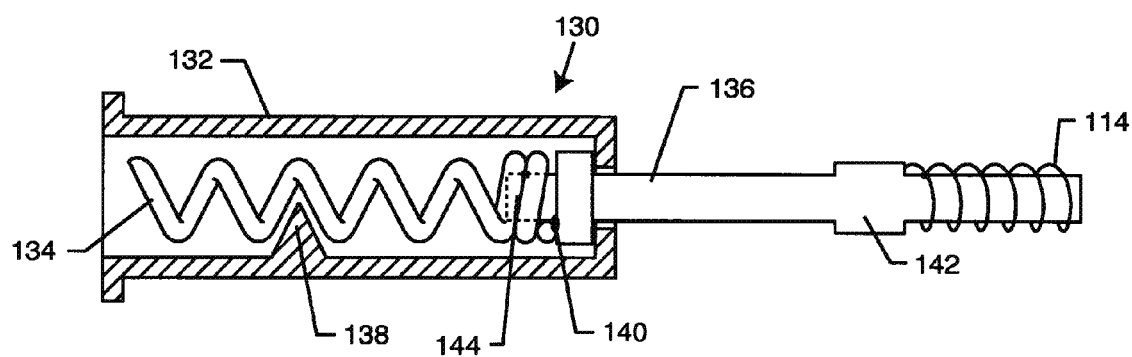
FIG. 7 is a cross-sectional view of a generic prior art active fixation distal tip typically used in conjunction with cardiac pacemakers.

FIG. 7 is a cross-sectional view of a generic prior art active fixation distal tip 130 which is typically used in conjunction with cardiac pacemakers. There is a metallic housing 132 which contains a sharp tipped distal helix coil 134. This helix coil 134 is shown in its retracted position, which enables the physician to insert the fixation tip assembly 130 endocardially through the venous system, through the atrium, and through the tricuspid valve into the right ventricle so it does not snag or tear any tissue, and is designed to be extended and screwed into myocardial tissue. Once it is in the appropriate position, the physician then turns leadwire spline assembly 136 in a clockwise rotation. This is done outside the pectoral pocket with the lead 114 protruding from the body. A torque tool is generally applied so that the physician can twist or screw the helix coil 134 into place. Protrusion 138 acts as a gear so that as helix coil 134 is turned, it is screwed forward. This makes for a very reliable fixation into myocardial tissue. The helix coil 134 is generally attached by a laser weld 140 to an end of the spline assembly 136 as shown. Attached to spline assembly 136, usually by laser welding, is the lead 114 coming from the AIMD. An optional feature 142 is placed on spline assembly 136 to create a positive stop as the physician is turning the leadwire assembly and screwing the helix coil 134 into body tissue. Of course, all of the materials of the active fixation tip 130 shown in FIG. 7 are biocompatible. Typically, the helix coil 134 is made of platinum iridium alloy and would be coated with various materials to improve electrical performance. The housing 132 would generally be composed of titanium or another equivalent biocompatible alloy. The spline 136 is generally a platinum iridium alloy.

Figure 8:
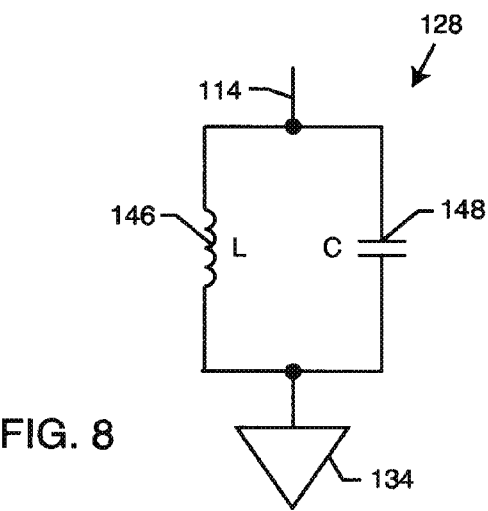
FIG. 8 is a schematic diagram of a distal Tip electrode tank circuit or bandstop filter.

FIG. 8 is the schematic diagram of a distal tip bandstop filter circuit 128 that can be inserted in series generally in location 144 in FIG. 7, as described in US 2007/0112398 A1. In order to do this, it is usually important that the inductor element L 146(L) and the capacitor element 148(C) be hermetically enclosed and also mechanically protected. Accordingly, they are typically installed in a hermetically sealed mechanically robust enclosure. However, these components must be very small in diameter to keep the lead and its associated distal tip small enough for insertion into various body tissues.

Figure 9:
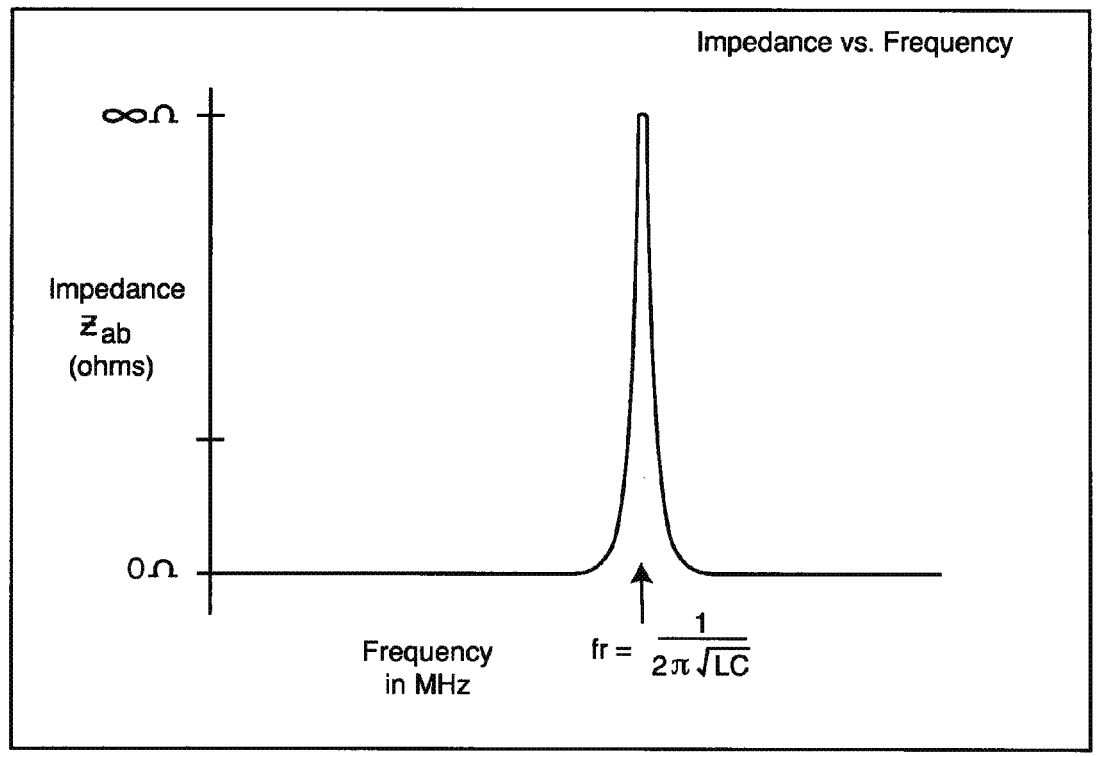
FIG. 9 is a graph showing impedance versus frequency for the parallel tank circuit of FIG. 8.

FIG. 9 is a graph showing impedance versus frequency for the ideal parallel bandstop filter circuit 128 of FIG. 8. As one can see, using ideal (zero resistance) circuit components, the impedance measured between the lead 114 and the helix coil 134 is zero until one approaches the resonant frequency $f_r$. At the frequency of resonance, these ideal components (the parallel inductor 146 and capacitor 148) combine together to approach an infinite impedance.

Figure 10:
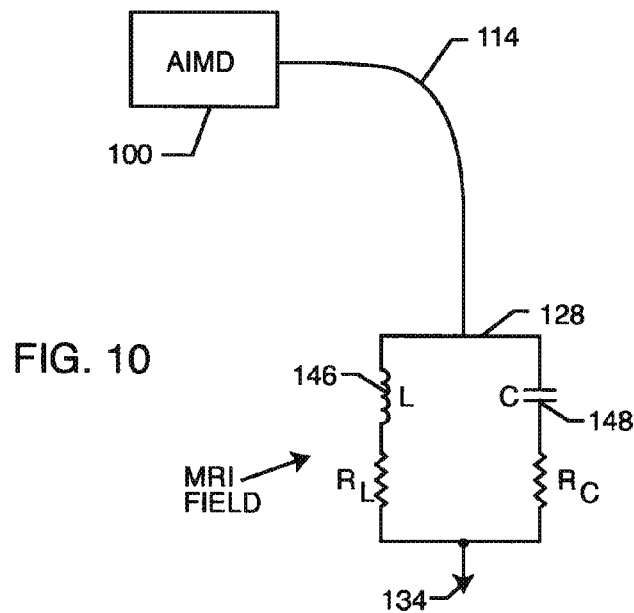
FIG. 10 is a schematic illustration of a unipolar AIMD lead system with a bandstop filter disposed near the distal electrode.

FIG. 10 is a drawing of a generic unipolar AIMD 100 and lead 114, with the bandstop filter 128 added at or near the distal electrode 134. The inductor 146 has a resistance element $R_L$ in series with it. The capacitor 148 also has a resistance $R_C$ in series with it. The resistances $R_L$ and $R_C$ can be separate discrete resistors or they are losses of the inductor and capacitor elements themselves. In general, the resistance $R_L$ will be the resistance of the circuit traces or wires used to form the inductor 146. The capacitor 148 has ohmic losses $R_C$ due to the resistance of its internal electrode plates, connection to its electrode plates, and dielectric losses. In the capacitor industry this is known as the capacitor's equivalent series resistance or ESR. The bandstop filter circuit 128 illustrated in FIG. 10 is a "real" bandstop filter in that the resistive losses are included. This makes it distinct from the ideal bandstop filter circuit 128 shown in FIG. 8. The presence of the bandstop filter 128 will present a very high impedance at a specific MRI RF pulse frequency to prevent currents from circulating through the distal electrode 134 into body tissue at this specific frequency.

Figure 11:
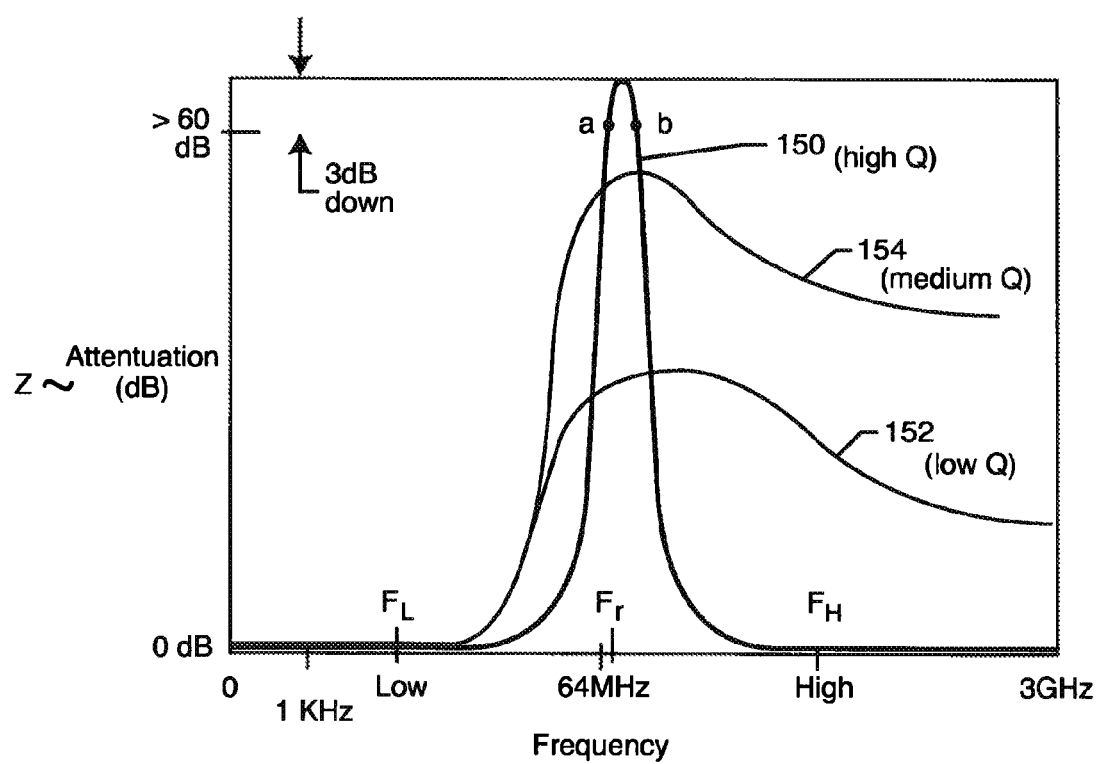
FIG. 11 is a graph of attenuation versus frequency for capacitors having high, medium and low Q.

FIG. 11 is a family of curves 150, 152 and 154 which show the attenuation in dB versus frequency for the bandstop filters 128 of the present invention. Curve 150 represents the use of very high Q inductor and capacitor components. If the capacitor and the inductor were ideal, meaning that they would both have zero resistance, then there would be no 3 db bandwidth at all between points "a" and "b". However, since in the real world both the inductor and the capacitor do have losses, a 3 db bandwidth separation between points "a" and "b" is achieved. It is very important that there be suitable bandwidth for two reasons: one, the MRI machine has gradient fields which change the RF frequency. This is how the MRI machine selects a slice to image, for example, through the knee. It does this by modifying the 1.5 Tesla or main static field by using a gradient field. This causes the Lamor frequency to change. Accordingly, one can see that some bandwidth is required centered around the specified pulsed resonant frequency of the MRI equipment so that all of these frequencies are properly attenuated in an implanted lead. If one were to deliberately use an inductor with a very high DC resistance and a capacitor with very high ESR, this would result in very low Q components and the resulting attenuation curve 152. The low Q attenuation curve 152 attenuates over a very broad range of frequencies; however, the attenuation in dB has been sacrificed.

Attenuation curves 154 or 156 shown in FIG. 11 are generally preferred. One can do this by controlling the relative Q of the inductor and the capacitor components of the bandstop filter 128. In one embodiment, the Q of the inductor would be relatively low and the Q of the capacitor would be relatively high. This means that the inductor would have a relatively high internal resistance and the capacitor would have a relatively low equivalent series resistance. This is achieved by using multiple turns of relatively small wire to create a high DC resistance in the inductor, and by using multiple and robust electrode plates to keep the equivalent series resistance (ESR) of the capacitor relatively low. The overall Q of the bandstop filter is thus selected to balance impedance at the selected frequency versus frequency bandwidth characteristics. The values of the inductor and the capacitor selected are such that the bandstop filter 128 is resonant at a selected frequency, and preferably selected to attenuate current flow through the lead or electrode along a range of selected frequencies. Such a frequency or range of frequency may include an MRI pulsed frequency. Typically, the Q of the inductor is relatively low or moderate, and the Q of the capacitor is relatively high or moderate to select the overall Q of the bandstop filter. That is, the inductor has a relatively high resistive loss $R_L$, and the capacitor has a relatively low equivalent series resistance $R_C$.

Figure 12:
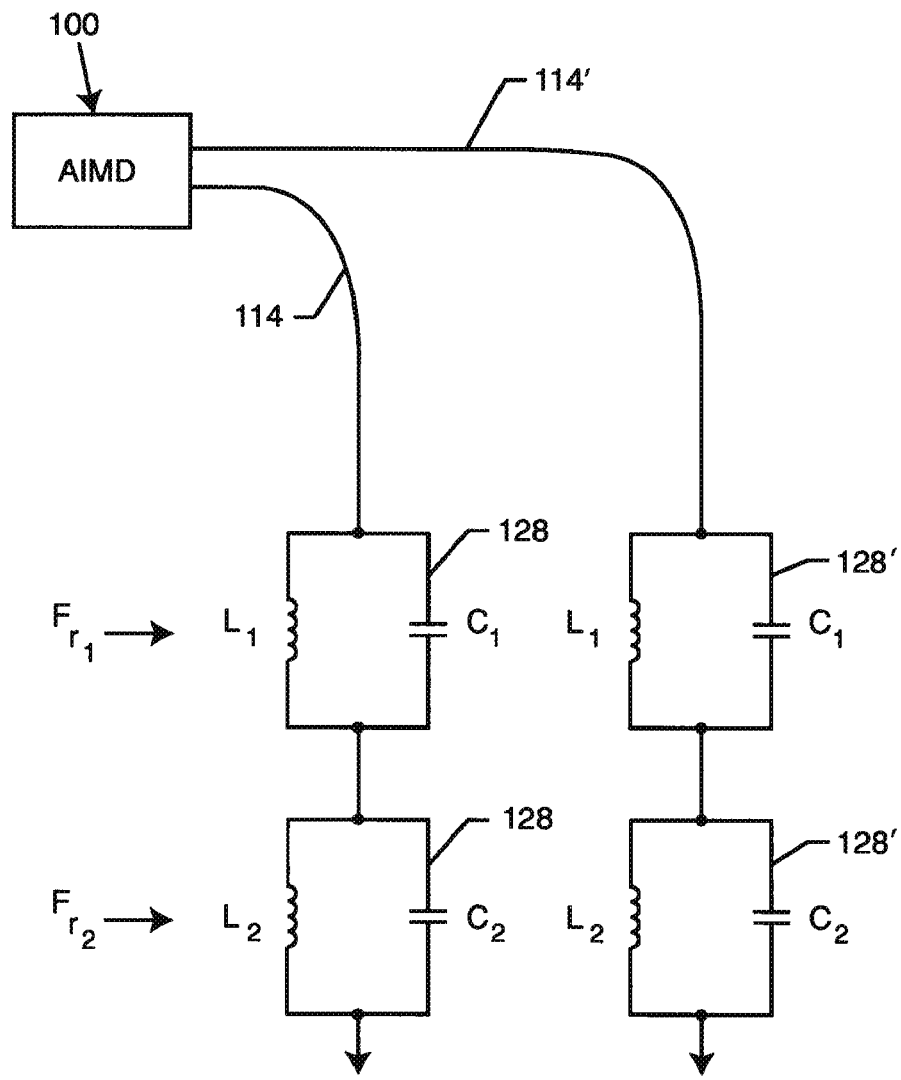
FIG. 12 is a schematic illustration of a bipolar AIMD wherein multiple bandstop filters are disposed in series with each one of the leads.

FIG. 12 illustrates a generic bipolar AIMD 100, meaning that it has two implanted leads 114 and 114'. Shown are multiple bandstop filters 128, 128' in series with each one of the leads 114 and 114'. For example, lead 114 has two bandstop filters 128 connected in series. As mentioned in US 2007/0112398 A1, these could be designed to resonate at two different frequencies, thereby providing attenuation to the RF pulse fields of both 1.5 Tesla and 3 Tesla MRI scanners. For example, the individual bandstop filters 128 in lead 114 could be designed to be resonant at 64 MHz ($Fr_1$) and 128 MH$_z$ ($Fr_2$), respectively. This would have the desired effect of having a high impedance at both of these common MRI RF pulsed frequencies thereby providing a high level of attenuation to RF induced currents at both 1.5 and 3.0 T. There could also be additional bandstop filters 128 if needed.

Figure 13:
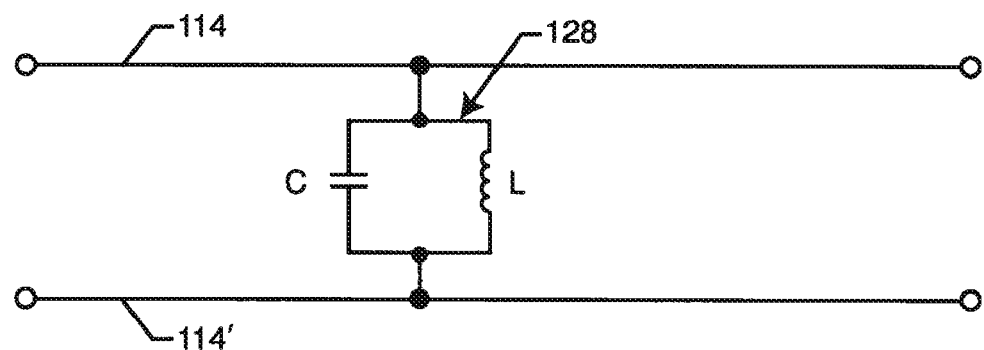
FIG. 13 is a schematic illustration of bipolar AIMD leads wherein a bandstop filter is disposed between the leads to form a diverter circuit.

FIG. 13 shows two circuit traces or leads 114 and 114', and the novel bandstop filter 128 of the present invention wired in parallel between the circuit traces or leads 114 and 114'. When the bandstop filter 128 is wired in parallel, instead of in series as shown FIGS. 6, 8, 10 and 12, the bandstop filter 128 becomes an RF current diverter instead of an RF current impeder. In FIG. 13, RF frequencies that form a voltage potential between circuit traces or leads 114 and 114' will all be diverted except at one frequency which is the resonant frequency of the bandstop filter 128. These types of circuits have broad utility in many types of radio applications or receiver applications, and many other types of electronic circuits used in the military, aerospace, and commercial markets.

As mentioned above, for medical implant applications it is very important that the implanted leads and their associated electrodes at the distal tips be very small. It is particularly important that the cross-sections or diameters of the bandstop filters be very small for easy endocardial insertion into the venous system of the human body. The present invention meets these criteria by using a novel combination of components that are mechanically mounted in series, but whose lumped elements are electrically in parallel. The components generally consist of commercial off-the-shelf miniature chip capacitor and inductor components. These are generally manufactured in high volume throughout the world. Accordingly, they are very inexpensive, but more importantly, they are very small in size. By way of example, a few years ago a small sized monolithic chip capacitor (MLCC) would be 0603, meaning that it would be 0.060 inch long by 0.030 inch in width. In comparison, today inductor and capacitor chip components can be purchased as small as 0201 or 01005. This means that they are so small that they literally can fit through a pepper shaker. Human hands cannot possibly handle components this small. Accordingly, micro-robotic manufacturing is the preferred method of manufacturing the novel components assemblies of the present invention, wherein the components typically are delivered on tape and reel and fed into the robots which pick and place the components and then go through a series of steps including additional component placement, wave soldering, cleaning, automatic optical inspection and automated electrical testing. All of this is done in a linear robotic manufacturing operation that is completely or nearly free of human hands. In cardiac rhythm applications (pacemakers and ICDs), a desirable lead size is 6 French (0.079 inches in diameter). For deep brain stimulator applications, an even smaller size is desirable, such as 3 French, which is 1 millimeter in diameter or 0.039 inches. US 2007/0112398 A1 discloses a number of methods of manufacturing novel bandstop filters for placement in the lead systems of active implantable medical devices. The present invention extends these concepts further.

In mammalian implant applications, the bandstop filters of the present invention should be small and placed in series with the implanted lead or electrode of the medical device. In such applications, it is necessary that the bandstop filter itself or a container therefor be biocompatible and highly reliable. Although commercial off-the-shelf capacitor and inductor components are very small in size, arranging them such that they are electrically coupled and likewise physically placed in parallel can increase the size of the bandstop filter where complications can arise in the placement and use of the implanted lead or electrode.

Commercial off-the-shelf capacitor and inductor components are typically not comprised of biocompatible materials. However, in accordance with the present invention, the inductor and capacitor elements can be constructed to be completely biocompatible. In this case it would be not necessary to place them in a biocompatible hermetic container. This would have great advantages in further reducing both size and cost. In this regard, US 2009/0116167, published May 7, 2009, and US 2009-0259265, published Oct. 15, 2009, are herein incorporated by reference.

Figure 14:
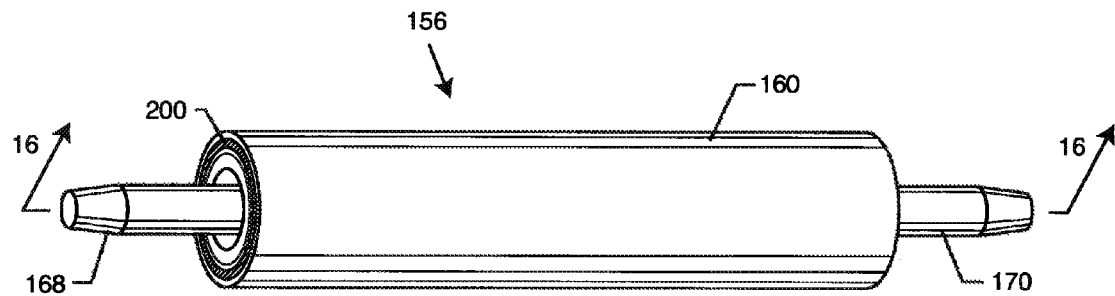
FIG. 14 is a perspective view of a hermetically sealed L-C bandstop filter assembly embodying the present invention.
Figure 15:
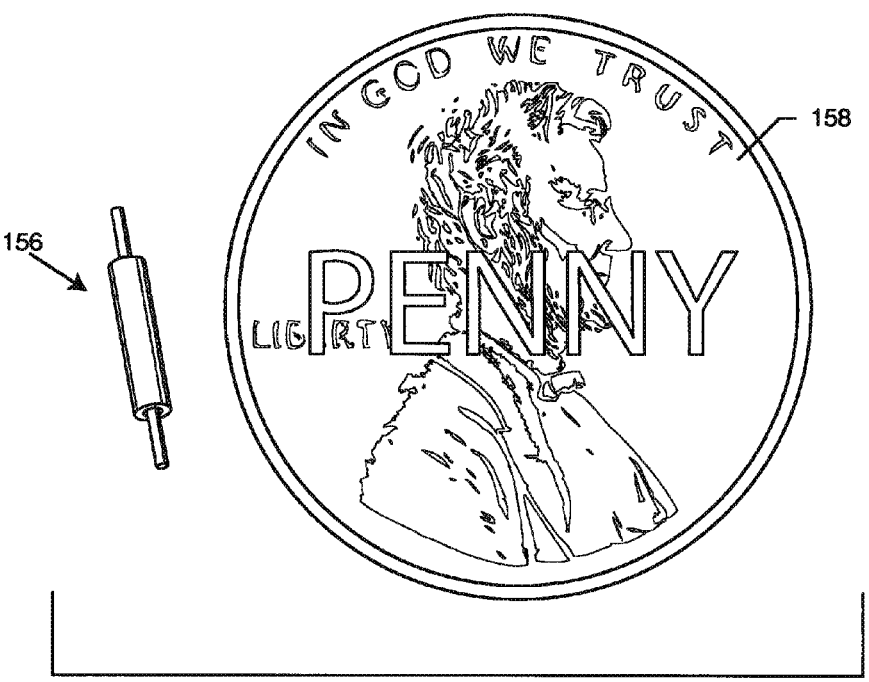
FIG. 15 is an illustration of how small the hermetically sealed assembly of FIG. 14 is in comparison with a U.S. one-cent coin.

With reference to FIG. 14, it is a feature of the present invention that custom or "off-the-shelf" non-biocompatible miniature inductor 146 and capacitor 148 components are mechanically installed in hermetic packages or containers 156 in series, but have electrical circuit traces that couple the lumped inductor and capacitor elements electronically in parallel, thereby forming bandstop filters 128 as described above. FIG. 14 illustrates an hermetically sealed container 156 having the inductor (L) and capacitor (C) components installed therein in series with one another, but whose lumped L and C elements are coupled electronically in parallel, so as to form one or more bandstop filters. The hermetically sealed container 156 is very small in diameter or cross-section and can be disposed between portions of an implantable lead 114, within an electrode assembly, etc. FIG. 15 shows the exemplary hermetically sealed container 156 adjacent to a United States penny or one-cent coin 158.

Figure 16:
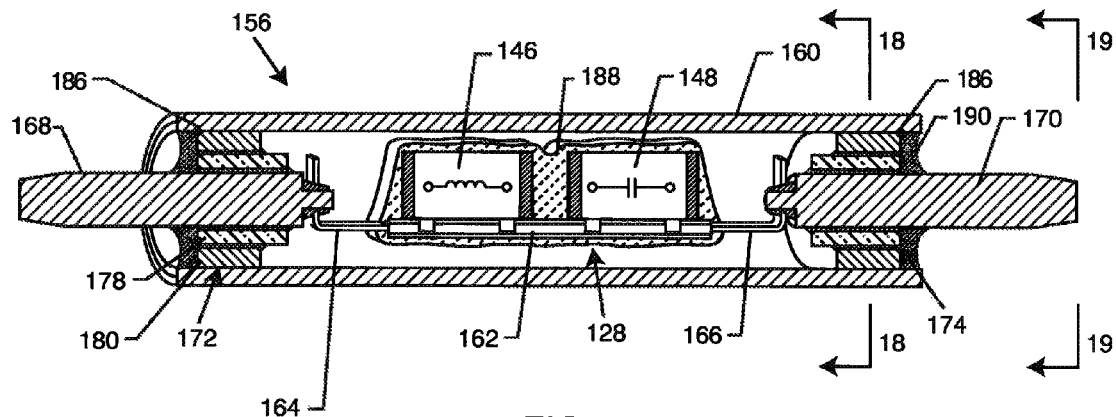
FIG. 16 is a cross-sectional view taken generally along the line 16-16 from FIG. 14.

FIG. 16 is a cross-sectional view taken generally along line 16-16 of FIG. 14 and shows the various component parts of the hermetically sealed container 156. The container 156 comprises a housing 160 which is biocompatible. By way of example, the housing 160 can be comprised of a biocompatible metal or alloy, such as titanium, platinum, platinum-iridium, gold, silver, etc., or a non-metallic material such as sapphire, ruby, alumina, ceramic, etc. The inductor 146 and the capacitor 148 are disposed on a substrate 162 and physically arranged in series, or end-to-end, with one another yet conductively or electronically coupled to one another in parallel. Circuit traces 164 and 166 are conductively coupled to the inductor 146 and capacitor 148 of the bandstop filter 128 and extend to conductive terminals 168 and 170 of hermetic seal assemblies 172 and 174. The conductive terminals 168 and 170 are designed to be conductively coupled to portions of the implantable lead 114 or electrode assembly, and that any conductive members which can be conductively coupled to the bandstop filter 128 within container 156 and extend therethrough in a hermetic fashion could be used.

Figure 17:
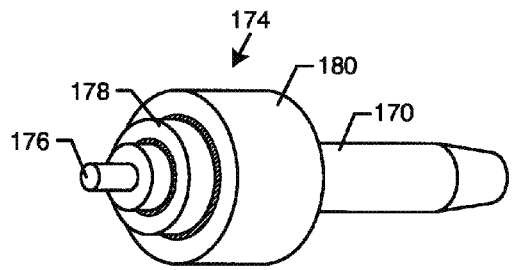
FIG. 17 is a perspective view of a hermetic terminal shown in FIGS. 14 and 16.

FIG. 17 is an enlarged perspective view of the hermetic seal assembly 174, having the terminal 170 extending therethrough to a crimp, solder joint or laser weld tip 176. The electrical connection to the tip 176 could also be formed by thermal-setting conductive adhesives. The terminal 170 is attached to an insulator 178, which is in turn attached to an outer ferrule 180.

Figure 18:
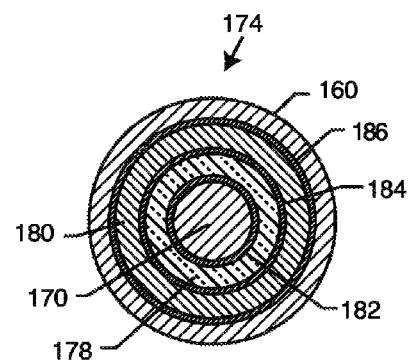
FIG. 18 is a sectional view of the hermetic terminal taken generally along the line 18-18 from FIG. 16.

FIG. 18 is a cross-section drawing taken along line 18-18 from FIG. 16. The terminal 170 is preferably of a common platinum-iridium alloy, such as 9010 or 8020. However, any biocompatible and suitable material could be used in place of platinum-iridium. Gold braze 182 forms a hermetic seal between terminal 170 and insulator 178. The insulator 178 may be a polished sapphire, ruby, polycrystalline alumina, or even glass or a general ceramic material. Sputtering would first be deposited on the surfaces so that the gold braze 182 will readily adhere and wet. Gold braze 184 forms a hermetic seal between insulator 178 and the ferrule 180. Gold brazes 182 and 184 are generally pure gold brazes for biocompatibility and long term reliability. The surface preparation process for the ceramic insulator 178 can be as follows: C-Axis single crystal, polycrystalline alumina (A12O3), Zirconia Stabilized Alumina and/or Yttria Tetragonal Zirconia Polycrystalline YTZP is etched using RF plasma before PVD sputtering using a biologically compatible metallic system. Plasma cleaning removes organic surface contamination and hydroxyl/oxides resulting in a higher energy surface. This activated surface readily forms strong covalent bonds with metallization atoms promoting robust, hermetic adhesion. Through industry standard process refinements, the resulting low stress, dense coating does not spall off or blister and improves the function and reliability of the final brazed joint. The outer ferrule 180 is also, preferably, of platinum-iridium since it's very easy to laser weld. It is also radio-opaque.

In the preferred embodiment, the insulator 178 would be a polished sapphire. It would then go through a plasma-etch process, such as a 500 watt plasma-etch, to increase its surface roughness. Titanium lignum metallization would be a preferred sputter material for adhesion and wetting of the associated gold braze pre-forms.

In FIG. 17, one can see that the interior tip 176 of the terminals 168 and 170 has been extruded to be fitted into an aperture, socket, etc. of the conductive substrate or circuit traces 164 and 166. Alternatively, the interior tip 176 may have an aperture therethrough so that a crimped connection can be formed between it and the conductive substrate or circuit traces 164 and 166, and subsequently laser welded. The method of attachment to the interior tip 176 will vary in accordance with the type of attachment desired to the internal circuitry of the bandstop filter 128. In any event, the conductive terminals 168 and 170 are conductively coupled to the bandstop filter 128 as the associated hermetic seal assemblies 172 and 174 are slid into place and hermetically sealed by laser welding 186 to the housing 160 of the container 156.

FIG. 16 shows the bandstop filter 128 comprised of the inductor 146 and capacitor 148, and the flexible circuit substrates 164 and 166 extending therefrom, attached to the terminals 168 and 170 so as to place the terminals 168 and 170 in electrical series with one another. However, the inductor 146 and the capacitor 148, although placed end-to-end and physically in series with one another, are conductively coupled electrically with one another in parallel. An insulating material 188, such as a thermal-setting non-conductive polymer, at least partially fills the remainder of the housing 160 to provide protection and mechanical robustness to the overall container assembly 156. This structure lends itself to a novel "ship-in-the-bottle" method of manufacturing. That is, all of the elements contained within the housing 160 are pre-assembled outside the housing. In particular, the terminal 168, the substrate 162 containing the inductor 146 and capacitor 148, and the opposite terminal 170 and the associated hermetic seals 172 and 174, are all pre-assembled outside of the overall housing 160. This facilitates proper electrical connections and electrical testing of the pre-assembly. In addition, this entire subassembly can go through high reliability screening. Typically, this would consist of thermal cycling or thermal shock followed by a burn-in, which means applying a relatively high voltage at elevated temperature to the circuit components and then exhaustive electrical test afterwards. Once all of this has been done, this entire pre-assembly is slipped inside the overall cylindrical housing 160 and then a final laser weld 186 is formed.

Figure 19:
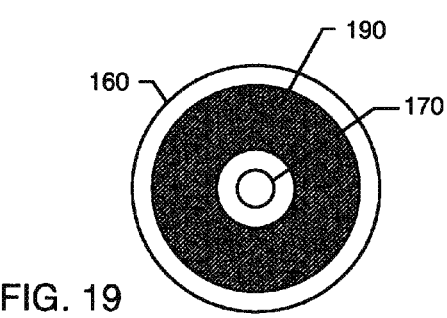
FIG. 19 is an elevational view taken generally along the line 19-19 from FIG. 16.

FIGS. 16 and 19 also show an optional conformal coating 190 which is provided over the two gold brazes 182 and 184. This conformal coating 190 could also be applied to the entire outer surface of the housing 160 and a portion of terminals 168 and 170, as well as optionally over the electrical attachments to the lead system. This conformal coating 190 is important to provide electrical isolation between the two terminals 168 and 170. When directly exposed to body fluids (which contain electrolytes), gold can migrate in the presence of a voltage bias. It has been shown that pacemaker pacing pulses in saline solution can actually cause a gold electromigration or electroplating action. The concern is that the gold braze materials 182 and/or 184, under voltage or pulse bias, may over time migrate or deposit (electro-plate) onto another surface such as the terminal 170 or the housing 160, which could negatively affect the long-term hermeticity and reliability of the hermetic seal assembly 174. Accordingly, the conformal coating or backfill 190 is placed as shown to cover both of the gold brazes 182 and 184. The conformal coating 190 may comprise thermal-setting non-conductive adhesives, silicones, parylene (which is vapor deposited), and the like, including epoxies, polyimides, polyethylene oxide, polyurethane, silicone, polyesters, polycarbonate, polyethylene, polyvinyl chloride, polypropylene, methylacrylate, para-xylylene, and polypyrrhol. In particular, Epo-tek H81 is considered a preferred epoxy which has already been tested for long-term biocompatibility.

A complete conformal coating 190 over the entire housing 160 may be desirable to provide electrical isolation between the conductive terminal pins 168 and 170. This provides critical performance capability in the event of complete saturation of the housing 160 in saline or biological fluid. See, for example, FIG. 45. Additional performance benefits for a conformal coating 190 include lubricity, radiopacity, and wear resistance.

Figure 20:
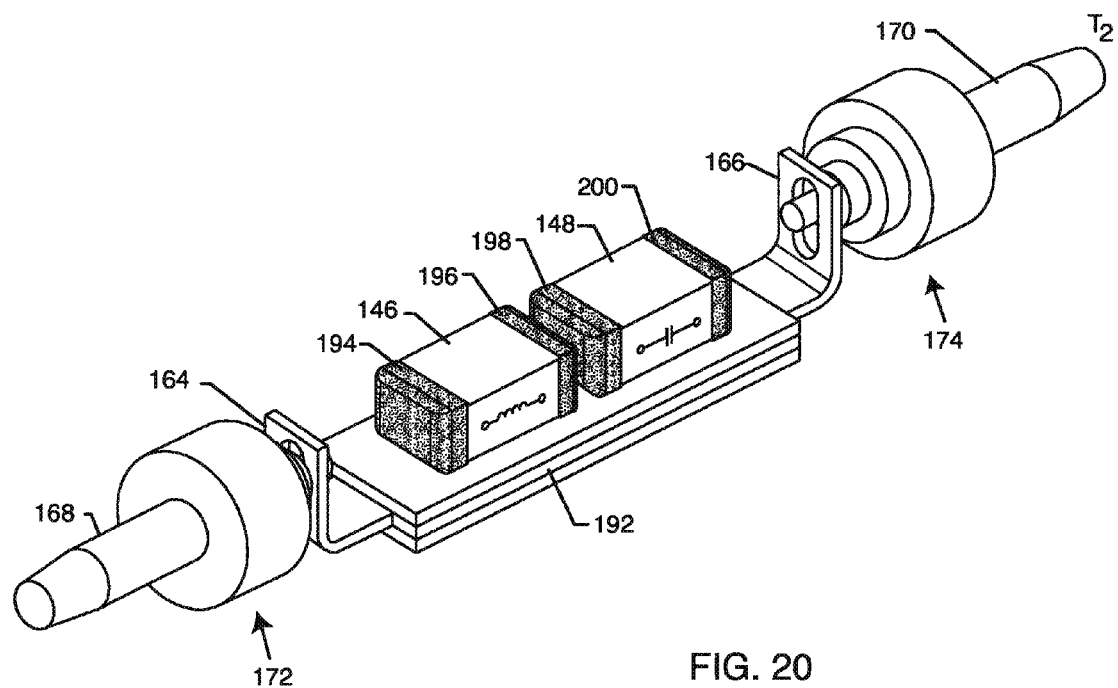
FIG. 20 is a perspective view illustrating a multilayer flex cable onto which a chip capacitor and a chip inductor are mounted in accordance with the present invention.
Figure 21:
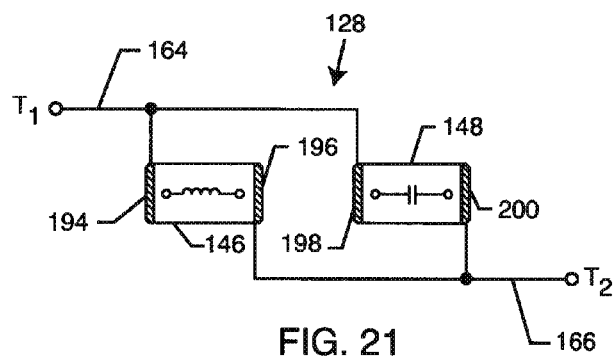
FIG. 21 is an electrical/physical schematic of the bandstop filter assembly of FIGS. 16 and 20, illustrating non-preferred conductive pathways and electrical connections to the serially arranged capacitor and inductor.
Figure 22:
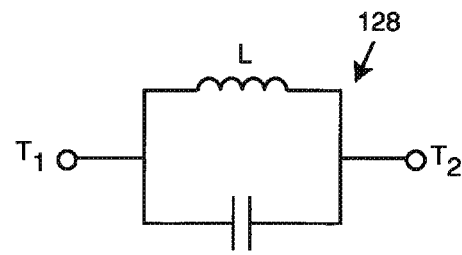
FIG. 22 is a purely electrical schematic of the bandstop filter of FIGS. 16 and 20.

FIG. 20 illustrates a multi-layer flex cable 192 onto which the inductor 146 and capacitor 148 are mounted. The inductor 146 is a chip inductor having first and second conductive termination surfaces 194 and 196 which are spaced from one another in non-conductive relation. The capacitor 148 also has first and second conductive termination surfaces 198 and 200 which are spaced apart from one another in non-conductive relation. The chip inductor 146 can be any number of chip inductor types, however the present invention is also not limited to chip inductors only. The inductor 146 could also be a solenoid inductor, a toroidal inductor, or any type of inductor that is known in the prior art. Moreover, the chip capacitor 148 can be any number of chip capacitor types, but the present invention is not limited to chip capacitors only. The capacitor 148 may be of many different types of capacitor technologies, including film capacitors, tantalum capacitors, monolithic ceramic capacitors, electrolytic capacitors, feedthrough-type capacitors, or even tubular capacitors. FIG. 20 shows that the inductor 146 and the capacitor 148 are physically disposed in series relative to one another, such that they are generally aligned with one another along a common longitudinal axis and placed end-to-end. However, in accordance with the present invention, the inductor 146 and the capacitor 148 are conductively or electrically coupled to one another in parallel. FIG. 22 is an electrical schematic diagram of the bandstop filter of FIGS. 20 and 21. When electrically connected as shown in FIG. 21, the second conductive terminal 196 of the inductor 146 is spaced a suitable distance away from the first conductive terminal 198 of the capacitor 148. The reason that these termination surfaces 196 and 198 must be placed apart is that in the presence of an MRI scanner, a substantial RF voltage can be generated across this gap. Arching or even short circuits may undesirably occur. Another concern is that a long term failure may occur due to the formation of metal dendrites or whiskers. This can happen even in the presence of a low voltage bias. However, having a large physical gap between the termination surfaces 196 and 198 is generally undesirable because it increases the overall length of the bandstop filter 128. As previously mentioned, the most critical dimension is the diameter. However, it is also important that the overall assembly not get too long.

FIG. 20 may be compared with FIG. 16 to see alternative configurations of the attachment between conductive terminals 168 and 170, and the conductive circuit traces or electrodes in 164 and 166. FIG. 16. illustrates a crimp configuration between the circuit traces or conductive substrates 164 and 166, and the respective tips 176 of the conductive terminals 168 and 170. In FIG. 20, an alternative configuration is shown wherein the hermetic seal assemblies 172 and 174 are pre-mounted to the conductive circuit traces or substrates 164 and 166, and attached thereto by resistance welding or the like.

Figure 23:
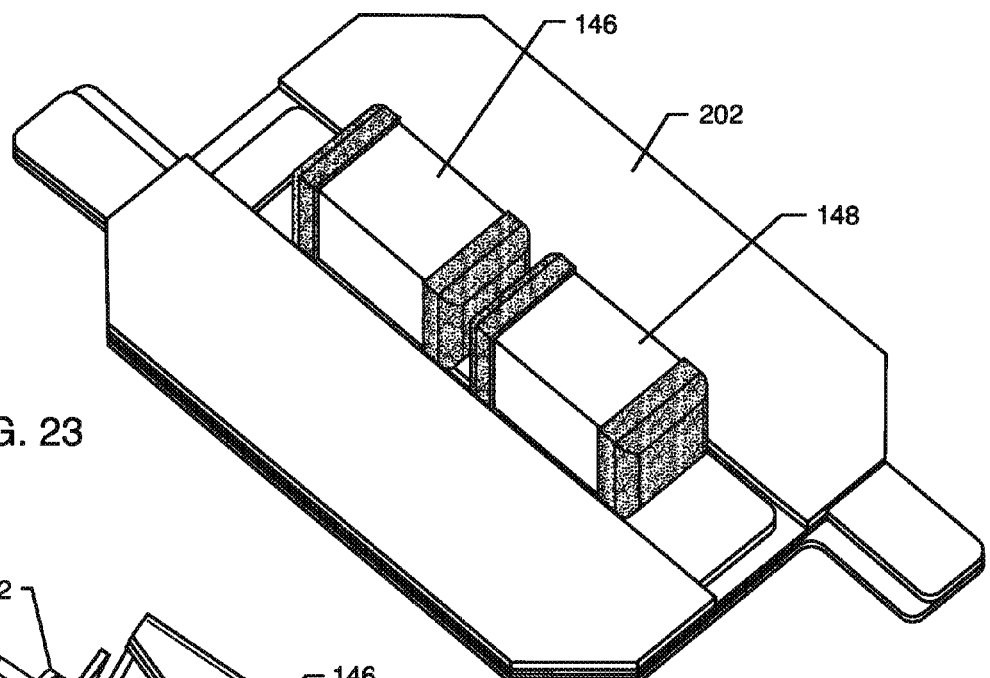
FIG. 23 is a perspective view of an alternative construction of the bandstop filter wherein the chip inductor and chip capacitor are mounted on a flexible circuit substrate.
Figure 24:
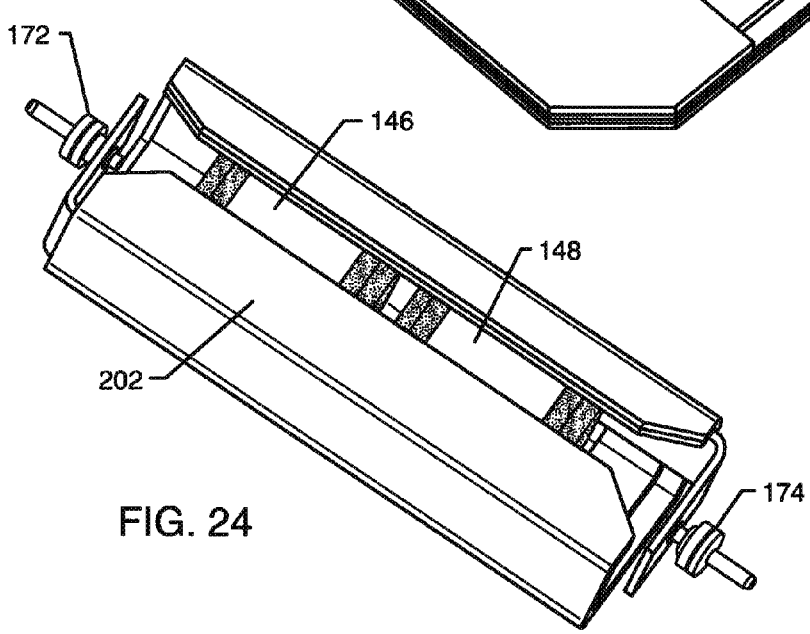
FIG. 24 is a perspective view of the assembly of FIG. 23, wherein the circuit substrate is folded up for insertion into a protective housing or container.

FIG. 23 illustrates an alternative embodiment wherein a flexible circuit substrate 202 is shown. For robotic manufacturing, it is highly desirable if the circuit substrate 202 be laying flat while the pick and place robots place the inductor 146 and the capacitor 148 components. The circuit substrate 202 includes portions which are conductive and other portions which are non-conductive, such that the conductive portions or traces of the substrate 202 place the inductor 146 and capacitor 148 in parallel electrical connection, although the inductor 146 and capacitor 148 are disposed generally end-to-end physically in series with one another. As illustrated in FIG. 24, the substrate 202 is then folded up so that it will fit conveniently into the cylindrical housing 160 as previously illustrated in FIG. 16.

Figure 25:
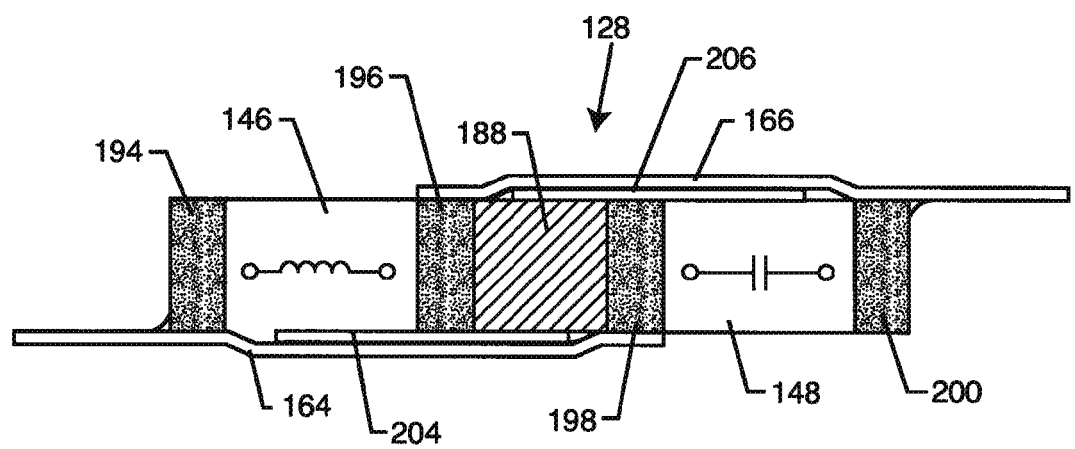
FIG. 25 is a top plan view of another alternative embodiment, wherein the serial inductor and capacitor are electrically connected in parallel in accordance with the non-preferred method shown in FIG. 21, and wherein an electrical insulator is disposed between adjacent ends of the inductor and the capacitor.

FIG. 25 shows another arrangement for an inductor 146 and a capacitor 148 physically disposed in series with one another in that they are arranged physically generally end-to-end, and yet the inductor 146 and the capacitor 148 are electrically connected in parallel to form a bandstop filter 128. A first conductive substrate or circuit trace 164 conductively couples the first conductive terminals 194 and 198 of the inductor 146 and the capacitor 148. An insulator 204 prevents conductive contact between the conductive substrate circuit trace 164 and the second conductive termination surface 196 of the inductor 146. Similarly, a conductive substrate or circuit trace 166 is conductively coupled to and extends between the second conductive termination surface 196 of the inductor 146 and the second conductive termination surface 200 of the capacitor 148. Another insulative layer 206 is disposed adjacent to the circuit trace or substrate 166 to prevent electrical contact between the first conductive termination surface 198 of the capacitor and the circuit trace or substrate 166. Conductive coupling can be by any known means, including solders or brazes. An insulator or insulating material is disposed between adjacent ends of the inductor 146 and the capacitor 148 to prevent arching or short circuits from developing between the adjacent conductive termination surfaces in the presence of, for example, an MRI scanner wherein a substantial RF voltage can be generated across this gap. The physical/electrical schematic model for the embodiment shown in FIG. 25 is illustrated in FIG. 21.

Figure 26:
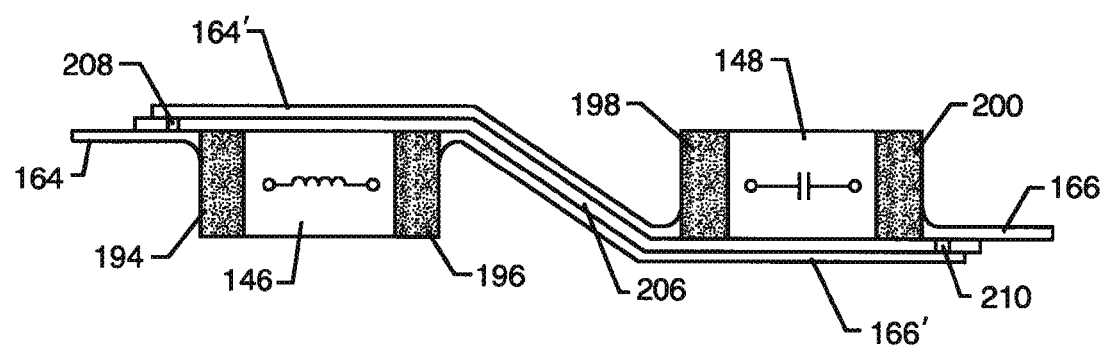
FIG. 26 illustrates yet another embodiment, wherein the serial capacitor and inductor are situated on opposite sides of an intermediate substrate.

FIG. 26 illustrates an alternative embodiment wherein the inductor 146 and the capacitor 148 are disposed on generally opposite first and second surfaces of a non-conductive substrate 206. Nonetheless, the inductor 146 and the capacitor 148 are generally arranged end-to-end and in series with one another. They are merely placed on opposite sides of the non-conductive substrate 206. A conductive substrate or circuit trace 164' extends from the first conductive terminal 198 of the capacitor 148 and is conductively coupled to a circuit trace 164 extending from the first conductive terminal 194 of the inductor 146 by means of a conductive connection through a passageway or through hole 208 extending through the non-conductive substrate 206. Similarly, a conductive substrate or circuit trace 166' extends from the second conductive terminal 196 of the inductor 146 across the non-conductive substrate 206 and is placed in conductive relation with the second conductive terminal 200 of the capacitor 148, such as by means of the conductive passage 210 which interconnects the circuit trace 166' with the circuit trace 166. The ends of circuit traces 164 and 166 can be coupled in series to the desired lead, electrode assembly, etc.

It will be appreciated that all of the assemblies illustrated in FIGS. 20-41 may be placed within a hermetically sealed container or package 156 so that off-the-shelf non-biocompatible inductor and capacitor components may be used. As such, conductive substrates, circuit traces or the like extending from the bandstop filter 128 will be conductively coupled to conductive contacts, such as terminals 168 and 170, extending through the housing 160 of the hermetically sealed assembly. In this manner, the hermetically sealed container 156 can be physically disposed in series between first and second portions of a lead or an electrode so as to place the bandstop filter 128 in series therewith.

Figure 27:
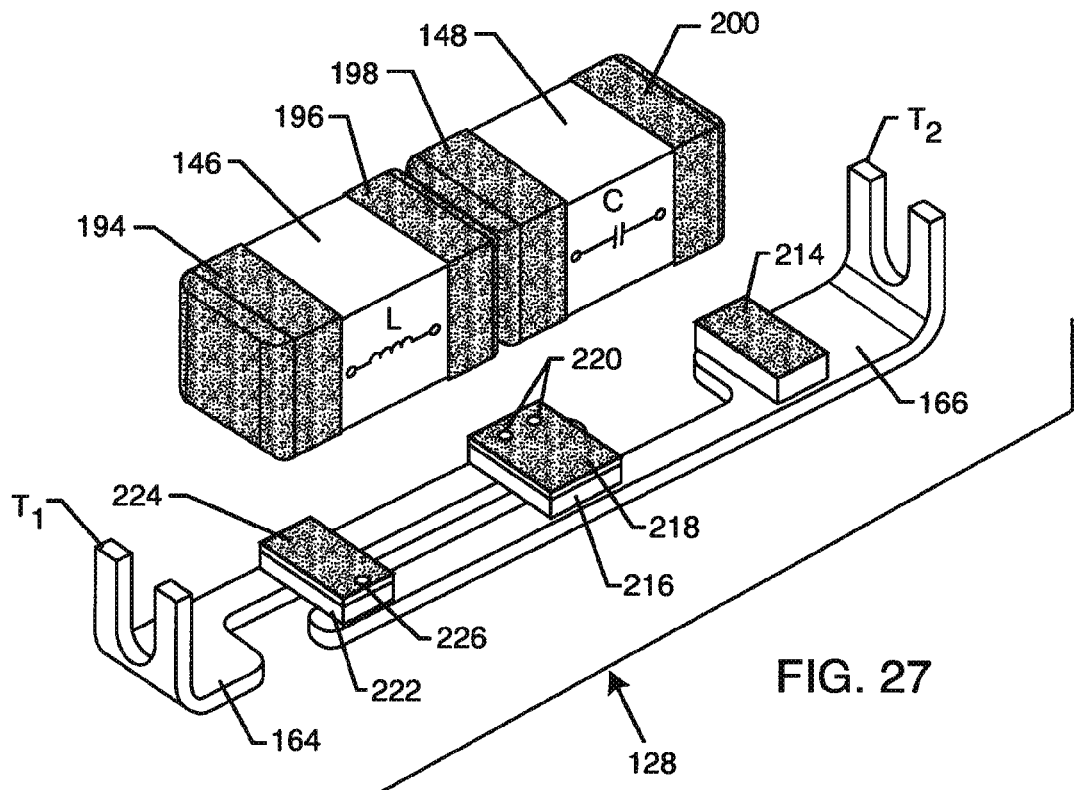
FIG. 27 is an exploded perspective view of the bandstop filter assembly of FIGS. 16 and 20, illustrating a preferred arrangement for electrically connecting the inductor and capacitor in parallel while they are physically arranged in series.
Figure 28:
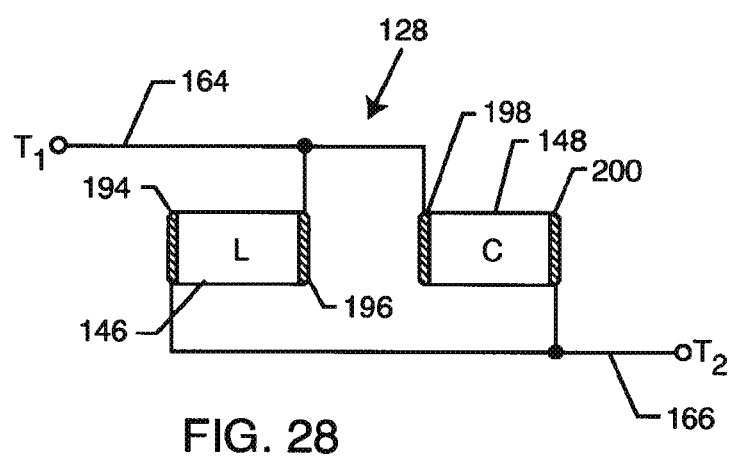
FIG. 28 is an electrical/physical schematic similar to FIG. 21, illustrating preferred conductor pathways and electrical connections to the serially arranged capacitor and inductor shown in FIG. 27.

FIGS. 27 and 28 are similar to FIGS. 20 and 21, but illustrate the preferred manner of electrically attaching the inductor 146 and the capacitor 148 in parallel while simultaneously arranging them physically in series, in accordance with the present invention. FIG. 27 differs from FIG. 20 in that the conductive circuit traces or substrates 164 and 166 are shown with much of the insulative and overmolding material of the substrate or flex cable 192 (FIG. 20) removed. Notably, the arrangement of components illustrated in FIGS. 27 and 28 requires no space between the inductor 146 and the capacitor 148, thus minimizing the longitudinal dimensions of the bandstop filter 128.

As seen best in FIG. 27, the second termination surface 196 of the inductor 146 is electrically shorted or at the same potential as the first termination surface 198 of the capacitor 148. By having a zero or nearly zero potential, there is no chance that arching, shorting or dendritic growth between these opposed surfaces 196 and 198. This also eliminates a space or gap between the inductor 146 and the capacitor 148. As shown in FIG. 27, a conductive bonding pad 214 is coupled to the conductive substrate 166 and conductively coupled to the second conductive terminal 200 of the capacitor 148. An insulative layer 216 extends between the circuit substrates 166 and 164. A conductive pad 218 comes into contact with conductive terminals 196 and 198 of the inductor 146 and the capacitor 148. Conductive passthroughs 220 extend from the conductive pad 218 through the insulative layer 216 and to the conductive circuit substrate 166 so as to place the conductive terminals 196 and 198 in conductive relation with each other and with the circuit trace or substrate 164. Similarly, a non-conductive insulation layer 222 extends between circuit substrates 164 and 166 and has a conductive pad 224 on an upper surface thereof which communicates with a conductive through hole 226 to the conductive substrate 164, so as to place the first conductive terminal 194 of the inductor 146 in conductive relation and connection with the circuit substrate 166.

This arrangement is diagrammatically illustrated the physical/electrical schematic of FIG. 28, wherein the capacitor 148 and inductor 146 are disposed physically in series with one another, but electrically and conductively coupled to one another in parallel. However, the entire bandstop filter, comprised of the capacitor 148 and the inductor 146 is in series with terminals $T_1$ and $T_2$, which could comprise the ends of the conductive substrates or circuit traces 164 and 166, the terminals 168 and 170, etc., so as to place the overall assembly in series with the implantable lead or electrode of a medical device. By carefully tracing each circuit, one can see that the inductor 146 ends up in parallel with the capacitor 148, forming a parallel resonant L-C bandstop filter 128, as illustrated in the electrical schematic drawing of FIG. 22.

There are particular challenges to designing and assembling components this small. Placing them in a hermetic package is even more challenging. In the present invention, a pre-assembly or subassembly may comprise the circuit traces, the inductor 146 and the capacitor 148 components, and the electrical connections. Then the hermetic seal assemblies 172 and 174 are attached to both ends of this rigid or flexible pre-assembly. This entire assembly is slid into a metallic tube or housing 160 (typically platinum or titanium), and then relatively low energy laser welds are used to make the final hermetic seal. The laser welds generally involve a spot size of 0.005 inches, which limits the amount of heating that's involved. This guarantees that the sensitive internal electrical connections and components will not be damaged.

Figure 29:
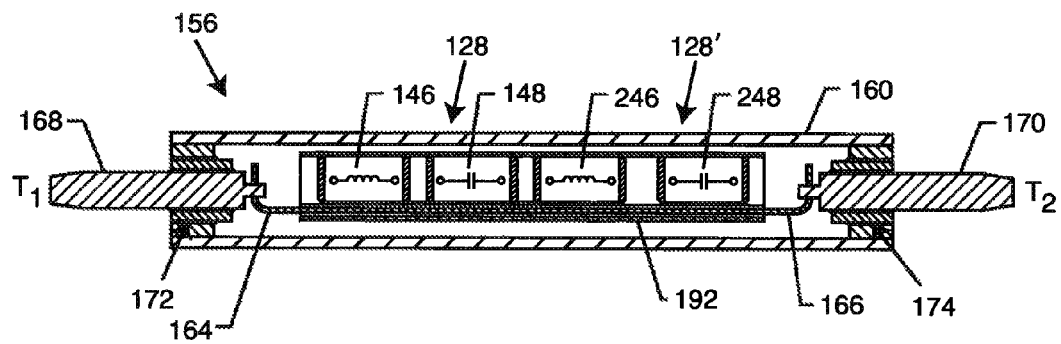
FIG. 29 illustrates another embodiment where two bandstop filters are placed in series with one another within a hermetically sealed container.
Figure 30:
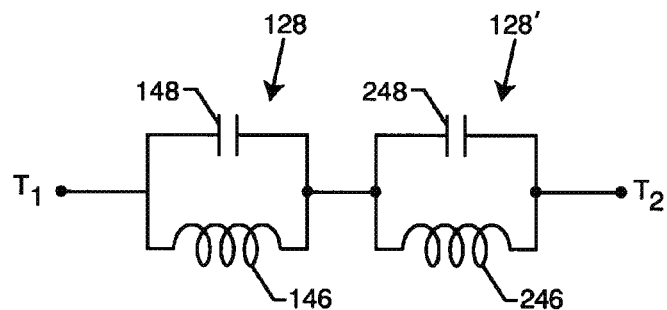
FIG. 30 is a purely electrical schematic of the dual bandstop filter assembly of FIG. 29.
Figure 31:
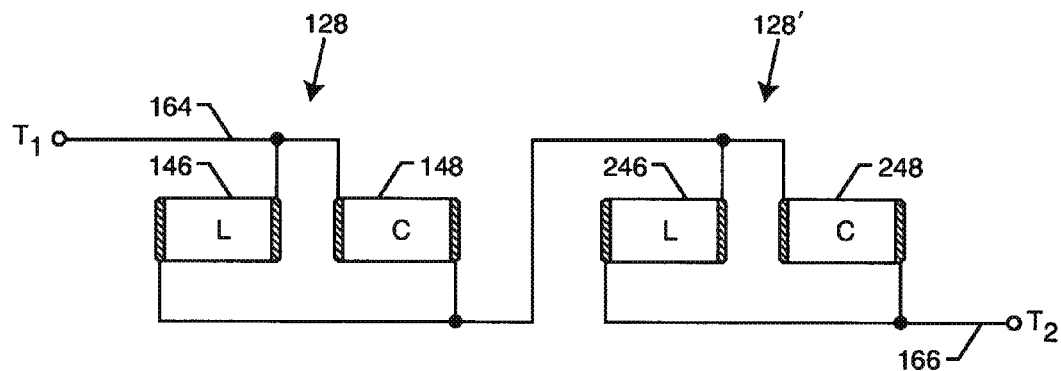
FIG. 31 is an electrical/physical schematic similar to FIGS. 21 and 28, illustrating preferred conductive pathways and electrical connections for the dual bandstop filter assembly of FIGS. 29 and 30.

FIGS. 29-31 illustrate a configuration where two bandstop filters 128 and 128' are placed in series. The first bandstop filter 128 consists of capacitor 148 and inductor 146. The second bandstop filter 128' consists of capacitor 248 and inductor 246. The first conductive substrate or circuit trace 164 cooperates with an intermediate internal circuit trace or conductive substrate (not shown) to conductively couple the capacitor 148 and the inductor 146 of the first bandstop filter 128 in parallel electrical relation with one another, and the second end circuit trace or conductive substrate 166 cooperates with the intermediate circuit trace or conductive substrate to place the capacitor 248 and the inductor 246 of the second bandstop filter 128' in parallel with one another such that the bandstop filters 128 and 128' are placed in series with one another. One can follow the conductive circuit paths within substrate 192 of each bandstop filter shown in FIG. 29, in the physical/electric schematic illustration of FIG. 31.

In a preferred embodiment, the bandstop filters 128 and 128' will be resonant at two different selective frequencies. For example, the first bandstop filter 128 could have a self resonant frequency at 64 MHz which corresponds with a 1.5 Tesla MRI machine. The second bandstop filter 128' could be resonant at 128 MHz which is the RF pulsed frequency of a 3 Tesla MRI system. Accordingly, by putting the two bandstop filters in series, the bandstop filter network of FIG. 29 would offer a high degree of attenuation to RF induced currents at both of these popular MRI frequencies.

However, the bandstop filters 128 and 128' can have the same resonant frequency or approximately the same resonant frequencies. The advantage of having two bandstop filters in series with approximately the same resonant frequency is that this increases the attenuation of the overall bandstop filter. By having the resonant frequencies of the bandstop filters 128 and 128' at slightly different frequencies, the resultant filter has the advantage of broadening the 3 dB bandwidth (see FIG. 11). An advantage of the configuration shown in FIG. 29 is that the slenderness ratio of the assembly can be maintained. That is, the overall diameter of the assembly must not be allowed to increase. Length is not nearly as critically important for an implantable lead, for example, for cardiac rhythm application, as is diameter. Also current handling ability is very important. By having two bandstop filters in series, one greatly increases the overall impedance and attenuation at resonance thereby providing a much higher level of protection to adjacent body tissues.

Figure 32:
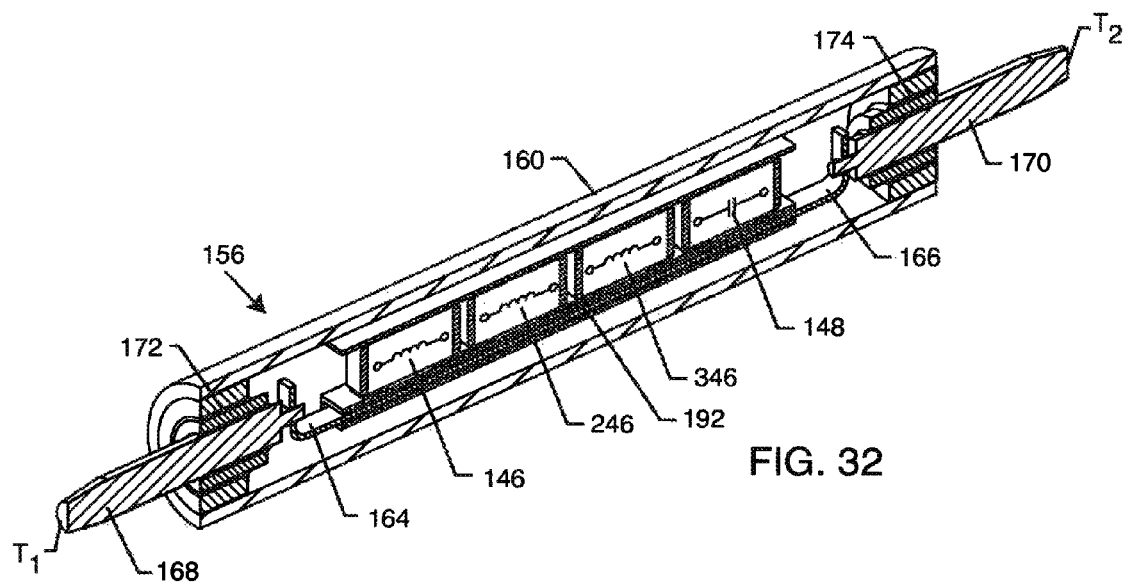
FIG. 32 is a perspective sectional view illustrating yet another embodiment where three inductors are physically placed in series with a single capacitor and yet electrically connected to the capacitor in parallel.
Figure 33:
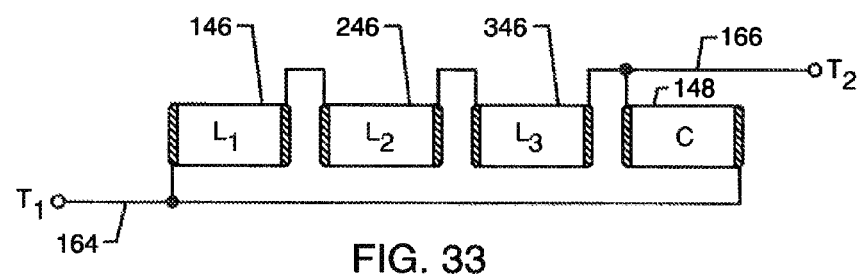
FIG. 33 is an electrical/physical schematic diagram of the connections between the inductors and the capacitors of FIG. 32.
Figure 34:
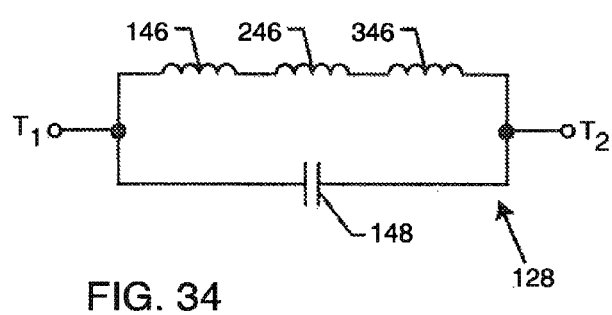
FIG. 34 is a purely electrical schematic of the assembly of FIGS. 32 and 33.

FIGS. 32-34 illustrate an alternative embodiment where three series inductors 146, 246 and 346 are placed in parallel with a single capacitor 148. It is well known in electrical engineering that when inductors are wired in series they add up. In other words, the total inductance is the sum of the three individual inductances. The three inductors 146, 246 and 346, which are in series are together in parallel with the capacitor 148, form the bandstop filter 128 as shown in FIG. 34. This arrangement has particular advantages for AIMD lead applications. This allows one to have a relatively high value of inductance while at the same time keeping the diameter or cross-sectional area very small. A disadvantage of this arrangement is that the resistive losses of the three inductors add up in series. This makes the bandstop filter Q a little lower, tends to widen its 3 dB bandwidth, but also reduces its attenuation. The current handling ability, such as during an automatic external defibrillation pulse, is also slightly compromised by the added series resistance. Conversely the current handling ability and/or the bandstop filter Q can be improved by using a larger wire/trace/pathway diameter or width. The reduction on inductance per component, compared to an inductor with the same length utilizing a smaller wire/trace/pathway diameter or width, can be compensated by the increased number of inductors. Of course one will appreciate that the three series inductors can be replaced with two inductors, four inductors or more, all wired in series and then placed in parallel with the capacitor 148 to form a bandstop filter 128 having the desired characteristics.

Figure 35:
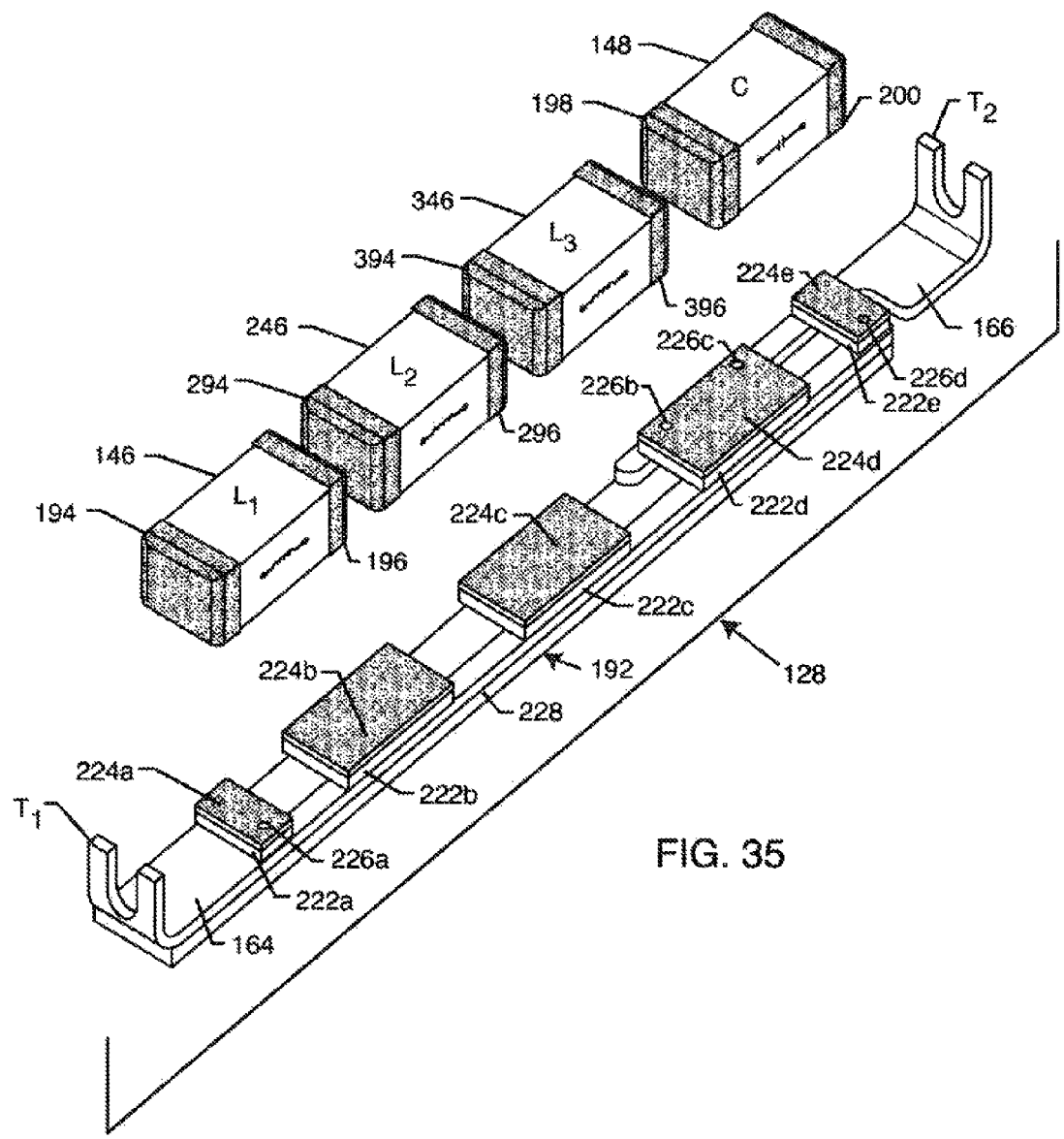
FIG. 35 is an exploded perspective view of the assembly of FIG. 32.

FIG. 35 is an exploded perspective view of the electrical subassembly of FIG. 32. Here, one can see that it has the same circuit substrate 192 that was shown in FIG. 32, which includes an insulative layer 228. It will be appreciated that much of the insulation forming a portion of the circuit substrate 192 has been removed in FIG. 35 to better illustrate the electrical circuit traces or substrates which electrically connect the three inductors 146, 246 and 346 in series, and place them all electrically in parallel with the capacitor 148. In this regard, the conductive circuit trace or substrate 164 extends nearly the length of the entire subassembly so as to conductively couple two both the first termination surface 194 of the first inductor 146 and to the second termination surface 200 of the capacitor 148. This is accomplished by providing a conductive pad 224a atop an insulation layer 222a, and a conductive passthrough 226a. The first conductive termination surface 194 of the first inductor 146 is conductively coupled to the conductive pad 224a which, in turn, conductively couples said first termination surface 194 to the substrate 164. In like manner, the second termination surface 200 is positioned adjacent and conductively coupled to a conductive pad 224e which sits atop an insulative layer 222e. The conductive pad 224e is conductively coupled to the substrate 164 through a conductive through-hole 226d. In order to place the three inductors 146, 246 and 246 electrically in series, two conductive pads 224b and 224c are provided which are electrically isolated from the underlying substrate 164 by insulative layers 222b and 222c. The second termination surface 196 of the first inductor 146 rests atop and is conductively coupled to the conductive pad 224b as is the first termination surface 294 of the second inductor 246. This arrangement conductively couples the second termination surface 196 of the first inductor 146 to the first termination surface 294 of the second inductor 246. Similarly, the second termination surface 296 of the second inductor 246 rests atop a conductive pad 224c and is conductively coupled thereto, as is the first termination surface 394 of the third inductor 346. This arrangement conductively couples the second termination surface 296 of the second inductor 246 to the first termination surface 394 of the third inductor 346. Finally, the second conductive termination surface 396 of the third inductor 346 is conductively coupled to the first termination surface 198 of the capacitor 148 by means of a conductive pad 224*d* on which both termination surfaces rest and are conductively coupled thereto. This conductive pad 224*d* is situated atop an insulative layer 222*d* and is conductively coupled to the conductive circuit trace or substrate 166 by means of conductive through-holes or passageways 226*b* and 226*c*.

Figure 36:
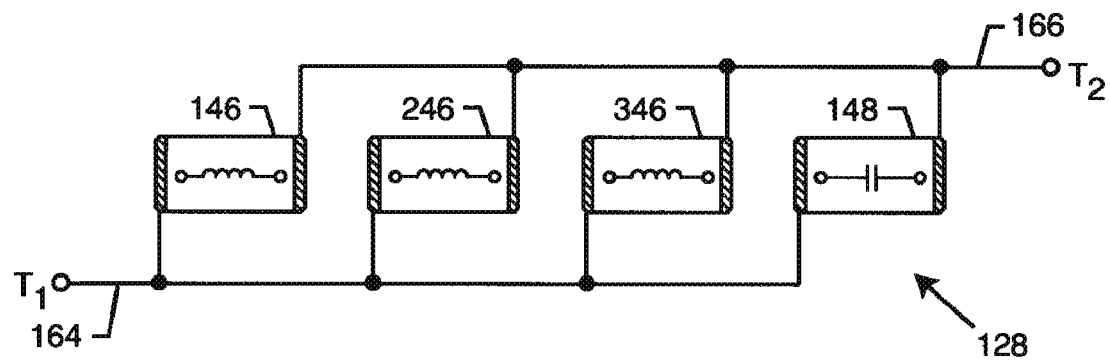
FIG. 36 is an electrical/physical schematic diagram similar to FIG. 33, but illustrating three inductors and a single capacitor all electrically conducted in parallel.
Figure 37:
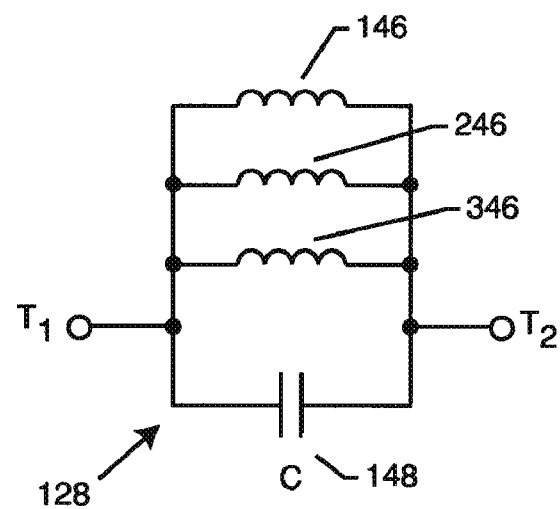
FIG. 37 is a purely electrical schematic of the assembly of FIG. 36.

FIGS. 36 and 37 illustrate yet another arrangement contemplated by the present invention, wherein the three inductors 146, 246 and 346 are placed in series with one another physically, but coupled conductively with one another in parallel. The capacitor 148 is also conductively coupled with the inductors 146, 246 and 346 in parallel to create a bandstop filter 128.

Figure 38:
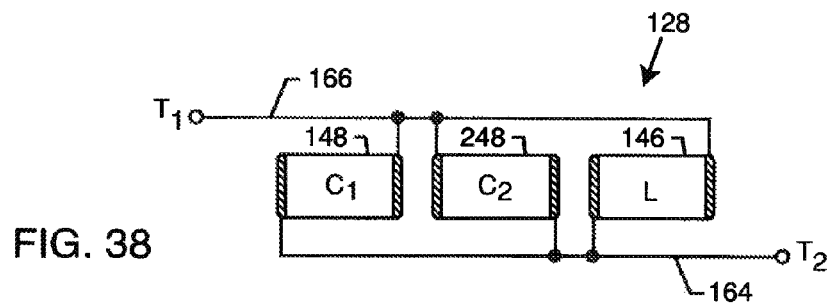
FIG. 38 is an electrical/physical schematic diagram similar to FIGS. 33 and 36, but illustrating two capacitors and a single inductor all electrically connected in parallel.
Figure 39:
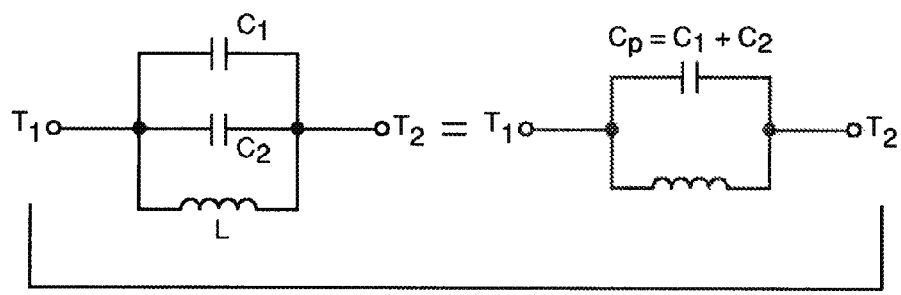
FIG. 39 are equivalent electrical schematics for the assembly of FIG. 38.
Figure 40:
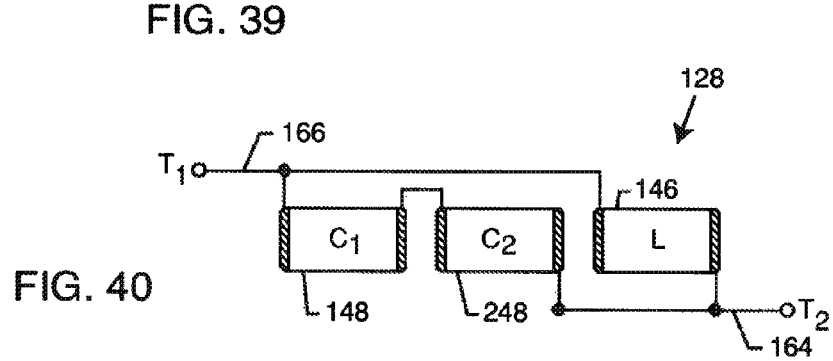
FIG. 40 is an electrical/physical schematic diagram similar to FIG. 38, but illustrating two capacitors electrically connected in series, and then collectively electrically connected in parallel with a single inductor.
Figure 41:
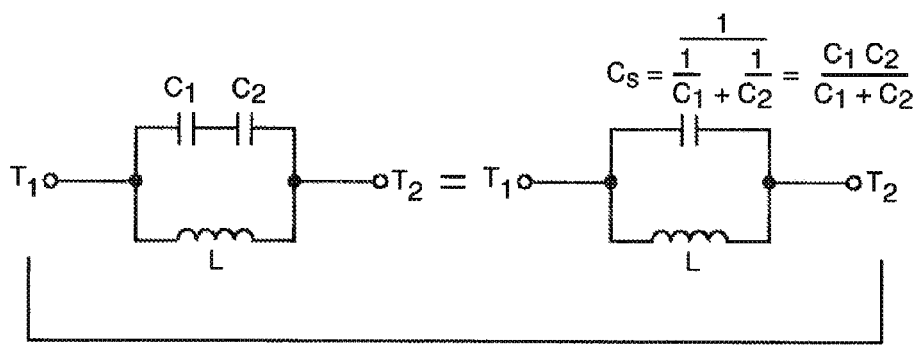
FIG. 41 are equivalent electrical schematics for the assembly of FIG. 40.

FIGS. 38 and 39 illustrate another arrangement contemplated by the present invention, wherein two capacitors 148 and 248 are placed in series with one another physically but coupled conductively with one another in parallel. The capacitors are also conductively coupled with the inductor 146 in series to create a bandstop filter 128. Yet another alternative is illustrated in FIGS. 40 and 41, wherein the capacitors 148 and 248 are disposed physically in series with one another and conductively coupled to one another in series, yet conductively coupled to the inductor L in parallel to form a bandstop filter 128. In both of these latter two embodiments, the capacitors 148 and 248 and the inductor 146 are placed end-to-end and generally disposed in series with one another yet still form a bandstop filter without increasing the overall diameter of the assembly. Thus, it will be appreciated that different values of the bandstop filter 128 may be obtained by placing multiple capacitors or inductors physically in series with one another, but in various combinations of electrical and parallel coupling to achieve the desired values.

Figure 42:
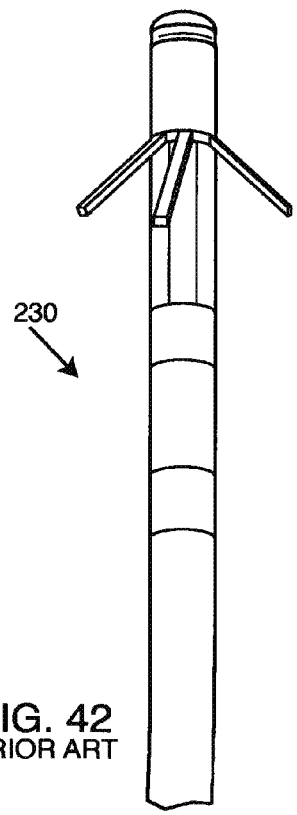
FIG. 42 is a fragmented perspective view of a passive electrode typically used in cardiac pacemaker applications.
Figure 43:
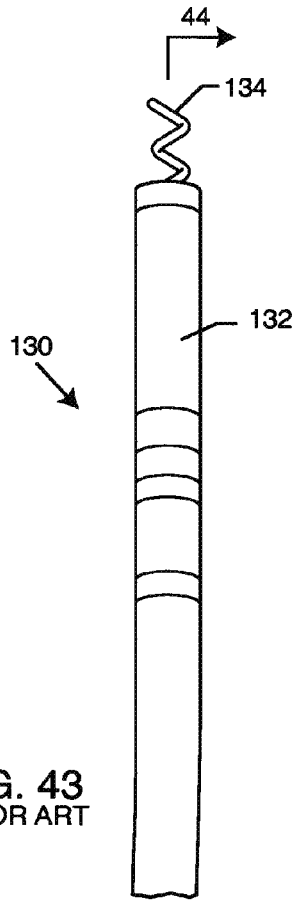
FIG. 43 is a fragmented perspective view of an active fixation tip.

With reference now to FIG. 42, a passive electrode 230 typically used in cardiac pacemaker applications is shown in which the hermetically sealed bandstop filter assembly of the present invention can be incorporated. FIG. 43 illustrates an active fixation Tip electrode 130 having a helix screw 134 selectively extendable and retractable from the lead housing 132. The helix screw 134 is retracted while the lead housing 132 is inserted endocardially to the correct location, for example, into the right ventricle. The physician then uses a tool (not shown) in the pectoral pocket and twists this entire assembly which literally screws the distal helix screw 134 into the myocardial tissue.

Figure 44:
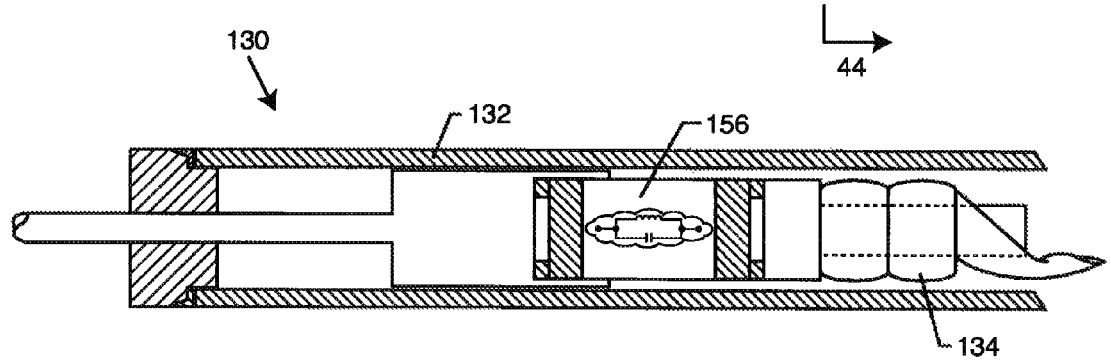
FIG. 44 is an enlarged, fragmented sectional view taken generally along the line 44-44 from FIG. 43, illustrating placement of a bandstop filter in accordance with the present invention in series with an electrical lead for a medical device.

FIG. 44 is a cross-section taken along line 44-44 from FIG. 43. Shown is the hermetically sealed bandstop filter assembly 156 that is embedded within the overall lead housing 132. The hermetically sealed bandstop filter assembly 156 can be as the assembly illustrated in FIGS. 14 and 16, or any of the other variations illustrated herein or contemplated by the present invention. The important aspect is that the various inductor and capacitor components be physically disposed in series relative to one another, yet conductively coupled in parallel to form one or more bandstop filters which are hermetically sealed in a biocompatible container for insertion into the electrode or leadwire of the medical device.

Figure 45:
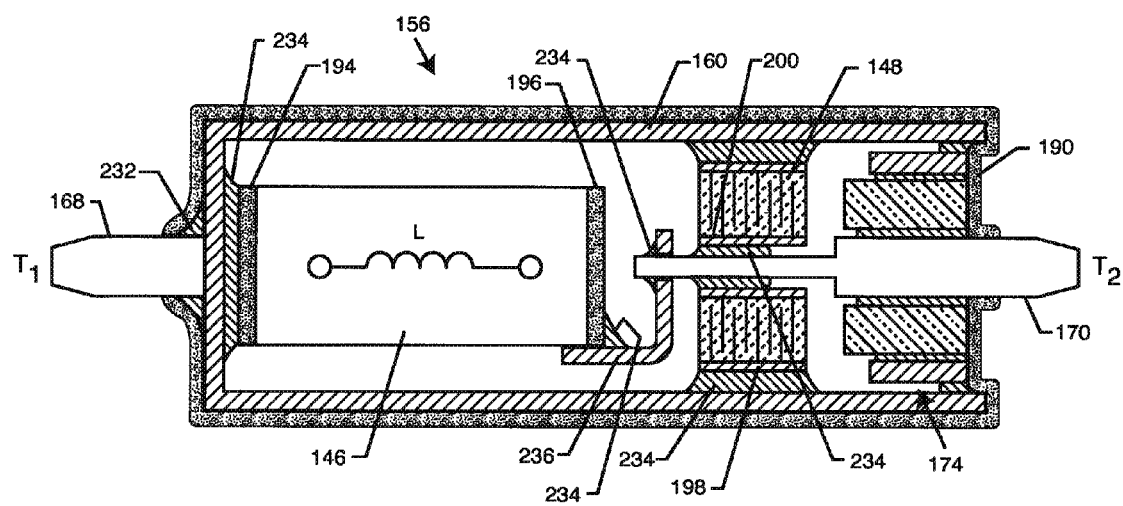
FIG. 45 illustrates another embodiment where a chip inductor and a feedthrough capacitor are placed in series within a hermetically sealed container.
Figure 46:
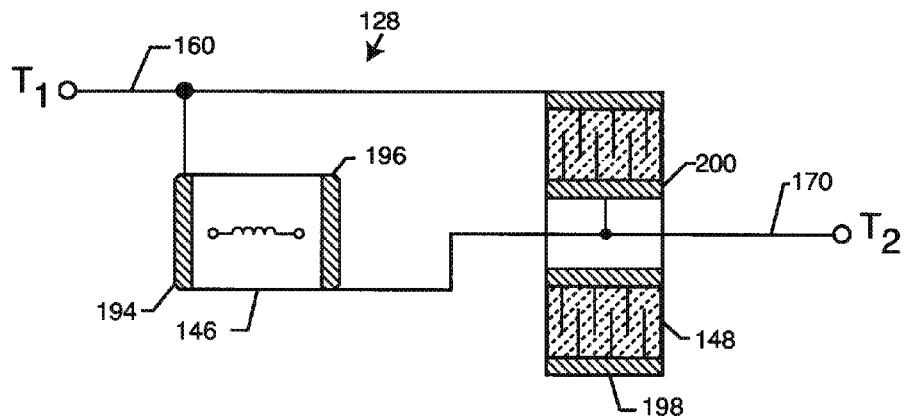
FIG. 46 is an electrical/physical schematic similar to FIGS. 21 and 28, illustrating conductive pathways and electrical connections for the bandstop filter assembly of FIG. 45.
Figure 47:
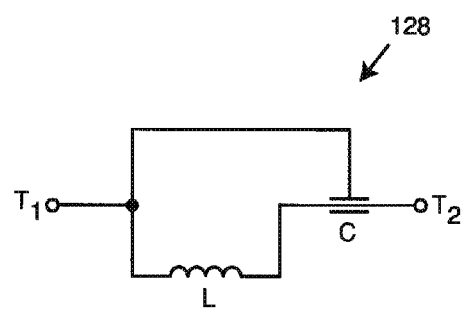
FIG. 47 is a purely electrical schematic of the bandstop filter assembly of FIGS. 45 and 46.

FIGS. 45-47 illustrate a configuration where a chip inductor 146 is physically disposed in series with a feedthrough capacitor 148, and yet is electrically connected in parallel to form a bandstop filter 128. The chip inductor 146 and the feedthrough capacitor 148 are disposed within a hermetic container 156 comprising a housing 160 of a biocompatible material which includes one open end, and a hermetic seal assembly 174 disposed within the open end of the housing 160. The conductive terminal 168 is conductively coupled to the housing 160 by a laser weld 232. The first conductive termination surface 194 of the inductor 146 is conductively coupled to the housing 160 by means of a conductive adhesive 234 or the like. The second conductive termination surface 196 of the inductor 146 is similarly conductively coupled by means of a conductive adhesive 234 or the like, to a conductive bracket 236 which is also conductively coupled to an extension 238 of the conductive terminal 170 which extends through a central passageway of the feedthrough capacitor 148. The first conductive termination surface 198 of the capacitor 148 is conductively coupled to the housing 160 by means of conductive adhesive 234 or the like, and the second conductive termination surface 200 of the feedthrough capacitor 148 is conductively coupled to the extension 238 of the conductive terminal 170 by means of conductive adhesive 234 or the like. The hermetic seal assembly 174 disposed within the opening to the housing 160, and which prevents direct contact between body fluids and the inductor 146, the capacitor 148 and related electrical components, is essentially the same as the hermetic seal assembly 174 illustrated in FIGS. 16-19. The illustrated structure advantageously eliminates one hermetic seal assembly in comparison with previously illustrated embodiments, by providing a terminal 168 which is shorted to the housing 160. As shown, the conformal coating 190 is applied over the entire outer surface of the housing 160 as well as a portion of the terminals 168 and 170. This conformal coating 190 advantageously provides additional electrical isolation between the two terminals 168 and 170.

Accordingly, from all of the foregoing it will be appreciated that the present invention relates to passive bandstop filter circuits wherein one or more of both inductor 146 and capacitor 148 elements are physically disposed in series but whose equivalent (lumped) L-C parameters are electrically connected in parallel. The disclosed embodiments are particularly suitable for applications where it is important to keep the diameter or cross-sectional area of the bandstop filter 128 relatively small as, for example, in medical implanted leads. Providing bandstop filters in such medical implanted leads serves to reduce the amount of radio frequency (RF) current associated heating due to energy deposited on the leads during medical diagnostic procedures, such as magnetic resonance imaging (MRI). The bandstop filter 128 may be designed to be resonant at the MRI RF pulsed frequency and thereby present a high impedance in the lead thus reducing RF current flow.

Although several embodiments have been described in detail for purposes of illustration, various modifications may be made without departing from the scope and spirit of the invention. Accordingly, the invention is not to be limited, except as by the appended claims.

What is claimed is:

1. A lead wire system for use with an active implantable medical device, the lead wire system comprising:
   a) an implantable lead comprising at least one lead wire having a length extending to and meeting with a proximal lead end and a distal lead end;
   b) a bandstop filter connected in series with the lead wire somewhere along the length thereof, the bandstop filter comprising a capacitor segment having a capacitor segment first end and a capacitor segment second end, and an inductor segment having an inductor segment first end and an inductor segment second end, wherein the capacitor segment first end is electrically conductively connected to the inductor segment first end, and the capacitor segment second end is electrically conductively connected to the inductor segment second end so that the inductor and the capacitor are electrically coupled to one another in parallel;

c) wherein the bandstop filter is electrically connected in series with the lead wire somewhere along the length thereof with one of the capacitor and the inductor residing at a proximal location along the length of the lead wire with respect to the other of the capacitor and the inductor residing at a distal location along the length; and d) wherein the inductor segment has an inductor segment inductance and an inductor segment resistance, and the capacitor segment has a capacitor segment capacitance and a capacitor segment resistance.

2. The lead wire system of claim 1 wherein a Q of the bandstop filter is reduced by either reducing the Q of the inductor segment inductance, reducing the Q of the capacitor segment capacitance, or both.

3. The lead wire system of claim 1 wherein the capacitor segment resistance is raised in order to reduce the Q of the capacitor segment.

4. The lead wire system of claim 1 wherein the Q of the bandstop filter circuit is reduced by increasing the capacitor segment resistance.

5. The lead wire system of claim 1 wherein a Q of the bandstop filter is such that its 3 db bandwidth provides attenuation across a range of MRI radio frequency (RF) pulse frequencies.

6. The lead wire system of claim 1 wherein the bandstop filter is disposed at, proximate to or within a distal end of the lead wire.

7. The lead wire system of claim 1 wherein the inductor segment does not comprise ferritic, ferrite or ferro-magnetic core materials.

8. The lead wire system of claim 1 wherein the capacitor segment comprises a ceramic capacitor.

9. The lead wire system of claim 1 wherein the lead wire has a wire structure selected from the group consisting of a spiral, coaxial, filer, bifilar and multifilar wire structure.

10. The lead wire system of claim 1 wherein the bandstop filter is biocompatible.

11. The lead wire system of claim 1 wherein the inductor segment is comprised of at least two series discrete inductors.

12. The lead wire system of claim 1 wherein the medical device is selected from the group consisting of a cochlear implant, a piezoelectric sound bridge transducer, a neurostimulator, a brain stimulator, a cardiac pacemaker, a ventricular assist device, an artificial heart, a drug pump, a bone growth stimulator, a bone fusion stimulator, a urinary incontinence device, a pain relief spinal cord stimulator, an anti-tremor stimulator, a gastric stimulator, an implantable cardioverter defibrillator, a pH probe, a congestive heart failure device, a pill camera, a neuromodulator, a cardiovascular stent, and an orthopedic implant.

13. The lead wire system of claim 1 wherein the inductor segment resistance, the inductor segment inductance, the capacitor segment capacitance, and the capacitor segment resistance result in a Q of the bandstop filter having a 3 db bandwidth on the order of megahertz.

14. The lead wire system of claim 13 wherein the 3 db bandwidth is tuned to a resonant center frequency as an MRI pulsed RF frequency.

15. The lead wire system of claim 1 wherein the bandstop filter is housed within a hermetically sealed biocompatible container.

16. The lead wire system of claim 15 wherein a ceramic insulator material is hermetically sealed between a ferrule and a terminal for the biocompatible container.

17. The lead wire system of claim 15 wherein the biocompatible container is provided with a conformal coating of a material selected from the group consisting of thermal-setting non-conductive adhesives, parylene, epoxies, polyimides, polyethylene oxide, polyurethane, silicone, polyesters, polycarbonate, polyethylene, polyvinyl chloride, polypropylene, methylacrylate, para-xylylene, and polypyrrhol.

18. The lead wire system of claim 1 wherein a cross section of the bandstop filter perpendicular to the length is 6 French, or less.

19. A lead wire system, which comprises:
a) at least one lead wire having length extending to and meeting with a proximal lead end and a distal lead end;
b) a bandstop filter connected in series with the lead wire and comprising a capacitor segment having a capacitor segment first end and a capacitor segment second end, and an inductor segment having an inductor segment first end and an inductor segment second end, wherein the capacitor segment first end is electrically conductively connected to the inductor segment first end, and the capacitor segment second end is electrically conductively connected to the inductor segment second end so that the inductor and the capacitor are electrically coupled to one another in parallel; and
c) wherein the bandstop filter is electrically connected in series with the lead wire somewhere along the length thereof with one of the capacitor and the inductor residing at a proximal location along the length of the lead wire with respect to the other of the capacitor and the inductor residing at a distal location along the length.

20. An active implantable medical device lead wire system, which comprises:
a) an implantable lead comprising at least one lead wire having a length extending to and meeting with a proximal lead end and a distal lead end;
b) a bandstop filter connected to the lead wire and comprising a capacitor segment having a capacitor segment first end and a capacitor segment second end, and an inductor segment having an inductor segment first end and an inductor segment second end, wherein the capacitor segment first end is electrically conductively connected to the inductor segment first end, and the capacitor segment second end is electrically conductively connected to the inductor segment second end so that the inductor and the capacitor are electrically coupled to one another in parallel;
c) wherein the bandstop filter is electrically connected in series with the lead wire somewhere along the length thereof with one of the capacitor and the inductor residing at a proximal location along the length of the lead wire with respect to the other of the capacitor and the inductor residing at a distal location along the length;
d) wherein the inductor segment has an inductor segment inductance and an inductor segment resistance, and the capacitor segment has a capacitor segment capacitance and a capacitor segment resistance; and
e) wherein the capacitor segment first end and the inductor segment first end are electrically conductively connectable to an external portion of a terminal pin of a hermetic seal, and the capacitor segment second end and the inductor segment second end are at the proximal end of the lead wire.

* * * * *